US011564556B2

(12) United States Patent
Farhadi

(10) Patent No.: US 11,564,556 B2
(45) Date of Patent: *Jan. 31, 2023

(54) ENDOSCOPE ACCESSORY

(71) Applicant: IzoMed, Inc., Irvine, CA (US)

(72) Inventor: Ashkan Farhadi, Irvine, CA (US)

(73) Assignee: IzoMed, Inc., Irvine, CA (US)

(*) Notice: Subject to any disclaimer, the term of this patent is extended or adjusted under 35 U.S.C. 154(b) by 378 days.

This patent is subject to a terminal disclaimer.

(21) Appl. No.: 15/338,194

(22) Filed: Oct. 28, 2016

(65) Prior Publication Data
US 2017/0065155 A1 Mar. 9, 2017

Related U.S. Application Data

(63) Continuation-in-part of application No. 14/575,509, filed on Dec. 18, 2014, now Pat. No. 9,480,390, and
(Continued)

(51) Int. Cl.
*A61B 1/00* (2006.01)
*A61B 1/015* (2006.01)

(52) U.S. Cl.
CPC ...... *A61B 1/00135* (2013.01); *A61B 1/00082* (2013.01); *A61B 1/00154* (2013.01); *A61B 1/015* (2013.01)

(58) Field of Classification Search
CPC ............ A61B 1/00082; A61B 1/00135; A61B 1/00154; A61B 1/015
See application file for complete search history.

(56) References Cited

U.S. PATENT DOCUMENTS 4,453,545 A * 6/1984 Inoue ................ A61M 16/0404
128/911
5,217,001 A * 6/1993 Nakao ................ A61B 1/00135
600/116
(Continued)

*Primary Examiner* — Matthew J Kasztejna
(74) *Attorney, Agent, or Firm* — Levine Bagade Han LLP

(57) ABSTRACT

This invention relates generally to a method for performing an endoscopic procedure.

According to some aspects of the invention, the method comprises placing an endoscope shaft within a body cavity at a desired examination point, the endoscope shaft having a proximal end, mid shaft and a distal end, the distal end terminating in an endoscope tip, wherein the endoscope tip is proximal to the desired examination point, positioning a segment of a longitudinally opened overtube over the endoscope mid shaft, wherein the overtube including a longitudinal reclosable seam along an entire length of the overtube, an inner surface, an outer surface, a proximal end and a distal end, a positioning ring adjacent the distal end on the outer surface, at least one sealing band on the inner surface, and an independently positionable occlusion catheter terminating in an asymmetrical occlusion balloon; at least one handle at the proximal end and on the outer surface for grasping and manipulation of the overtube within the body cavity. The method further comprises closing the seam of the segment of the overtube positioned over the endoscope mid shaft to form a longitudinally closed overtube and move the closed overtube over the endoscope shaft as guide within the body cavity and repeat the closing and moving till the overtube reaches the desired examination point, inflating the positioning ring to create a seal between the outer surface of the overtube and a body cavity proximal to the endoscope tip, wherein when inflated the positioning ring expanded asymmetrically around the overtube, inflating the at least one sealing band to create a seal between the internal surface of the overtube and endoscope shaft, passing the independently positionable occlusion catheter terminating in the
(Continued)

asymmetrical occlusion balloon through a passageway along the overtube to enter the body cavity at the end of the overtube, manipulating the independently positionable occlusion catheter to a selected point within the body cavity distal to the endoscope tip, inflating the occlusion catheter balloon to create seal between the occlusion catheter balloon and the body cavity, and creating a sealed examination compartment between the positioning ring, the asymmetrical occlusion balloon and the sealing band surrounding the distal end of the endoscope shaft.

20 Claims, 35 Drawing Sheets

Related U.S. Application Data a continuation-in-part of application No. 14/121,563, filed on Sep. 18, 2014, now Pat. No. 9,993,137, and a continuation-in-part of application No. 13/900,524, filed on May 22, 2013, now Pat. No. 9,521,945, and a continuation-in-part of application No. 12/266,953, filed on Nov. 7, 2008, now Pat. No. 9,867,529.

(56) References Cited

U.S. PATENT DOCUMENTS

| | | | | |
|---|---|---|---|---|
| 5,660,175 | A * | 8/1997 | Dayal | A61M 16/0404 128/207.14 |
| 6,234,958 | B1 * | 5/2001 | Snoke | A61B 1/303 600/114 |
| 6,440,061 | B1 * | 8/2002 | Wenner | A61B 17/3421 600/114 |
| 6,569,085 | B2 * | 5/2003 | Kortenbach | A61B 17/1285 600/104 |
| 6,585,639 | B1 * | 7/2003 | Kotmel | A61B 1/267 600/116 |
| 8,225,794 | B2 * | 7/2012 | Mikkaichi | A61B 1/015 128/207.14 |
| 2004/0221853 | A1 * | 11/2004 | Miller | A61M 16/0484 128/207.14 |
| 2006/0161044 | A1 * | 7/2006 | Oneda | A61B 1/00135 600/116 |
| 2009/0227835 | A1 * | 9/2009 | Terliuc | A61B 1/00082 600/106 |
| 2011/0251458 | A1 * | 10/2011 | Terliuc | A61B 8/445 600/116 |

* cited by examiner

ENDOSCOPE ACCESSORY

CROSS-REFERENCE TO RELATED APPLICATIONS

This application is a continuation-in-part of U.S. Ser. No. 14/575,509 filed on Dec. 18, 2014 and Ser. No. 14/121,563 filed on Sep. 18, 2014 and U.S. Ser. No. 13/900,524 filed on May 22, 2013 which is a continuation-in-part of U.S. Ser. No. 12/266,953 filed on Nov. 7, 2008, both of which are incorporated herein by reference.

I. FIELD OF INVENTION

Some embodiments of the present invention relates generally to the field of endoscopy and, more particularly, to an endoscope accessory for improving endoscopic examination of body organs, particularly the gastrointestinal tract.

II. BACKGROUND OF INVENTION

Endoscopy is a well-known procedure for examining the internal organs. The procedure is performed under the guidance of an endoscope. Currently used fiber optic endoscopes include lenses mounted in a flexible tube that relay an image from inside a body cavity for viewing by a physician for diagnosis or manipulation inside the body cavity.

In performing an endoscopy, it is common to insufflate (introduce air into) the gastrointestinal tract in order to provide easier visualization. This can cause bloating and discomfort to the patient or, in rare cases, severe abdominal pain.

More recently, echoendoscopy has been introduced. An echoendoscope (EUS) is a device that combines endoscopy and ultrasound to image the gastrointestinal wall and surrounding structures.

The ultrasound transducer is positioned at the distal tip of endoscope; the key components of the transducer are the piezoelectric crystals that vibrate to produce ultrasonic waves. The ultrasonic waves travel through the gastrointestinal wall and beyond the visceral wall into the surrounding organs. The reflection of these ultrasound waves is detected by the same crystals at the transducer and reconstruction of these reflections can result in creating a real time image of the gastrointestinal wall and its surrounding structures. The ultrasonic wave reflects from the surface of structures with different density and can pass very well through fluid containing and solid structures. Air, however, creates a barrier to ultrasonic wave passage and hampers the obtaining of ultrasonic images.

Several attempts have been made to minimize the amount of interfering air between the transducer and the examining structure. The prior art teaches the use of balloons at the end of the endoscope that encloses the transducer and is filled with water to permit acoustic coupling between the transducer and the luminal wall or other gastrointestinal structures. This is particularly helpful in the part of the gastrointestinal tract where the diameter of the lumen is small and the inflated balloon makes good circumferential contact with the intestinal wall and thus creates a good acoustic coupling. In most parts of the gastrointestinal tract, however, the large diameter of the lumen and/or the angle of the transducer in relation to the intestinal wall results in an inadequate contact between the transducer balloon and the intestinal wall. Therefore, operators usually use water infusion to fill the region of the gastrointestinal tract with water and create acoustic coupling between the transducer and the examined structures.

A significant shortcoming of this prior art is that it does not account for the fact that the gastrointestinal tract is not a closed region and the infused water soon moves to other regions of the gastrointestinal tract. Infusion of significant amounts of water during the examination could result in untoward problems such as aspiration of the water into the patient's airway or over distention of the gastrointestinal tract.

Further advances in the prior art include two-balloon approaches for assisting the movement of the endoscope. However, these prior art devices utilize the balloons only to secure and maintain positioning of the endoscope or to seal two separate anatomical structures from one another. To advance the endoscope, the balloons must be deflated and inflated in alternating order. Yet further attempts have taught the use of an overtube that consists of a device having a window near its distal end through which the endoscopic examination can be performed. A shortcoming of this approach is that it limits the maneuverability of the endoscope and may create noise, thereby diminishing the accuracy of a procedure.

There is need, therefore, for an examination accessory for endoscopic examination that creates an examination partition around the endoscope tip. Such a device can create an examination compartment proximal and distal to the endoscope or ultrasound tip. The examination compartment can then be filled with air, water or could be thoroughly lavaged using the device. Such a device can further include balloons comprising at least a positioning ring for maintaining the position of the endoscope accessory in an area to be examined and to seal the proximal end of the examination partition independent of the endoscope tip and can also include an independently positionable occlusion balloon distal to the tip of the endoscope or echoendoscope for sealing the distal end of the examination partition. There is further need for such a device that can be advanced or retracted without the necessity of deflating and re-inflating the balloons, thereby creating a movable examination compartment. There is further need for such a device that can be placed on an endoscope shaft without the necessity of having to remove the endoscope from the body. Some embodiments of the present invention provide such a device.

III. SUMMARY OF THE INVENTION

Some embodiments of the present invention improves endoscopic examination by enhancing and maintaining luminal view by deploying the proposed device. The endoscopic examination method comprises placing an endoscope shaft within a body cavity at a desired examination point, the endoscope shaft having a proximal end, mid shaft and a distal end, the distal end terminating in an endoscope tip, wherein the endoscope tip is proximal to the desired examination point, positioning a segment of a longitudinally opened overtube over the endoscope mid shaft, wherein the overtube including a longitudinal reclosable seam along an entire length of the overtube, an inner surface, an outer surface, a proximal end and a distal end, a positioning ring adjacent the distal end on the outer surface, at least one sealing band on the inner surface, and an independently positionable occlusion catheter terminating in an asymmetrical occlusion balloon; at least one handle at the proximal end and on the outer surface for grasping and manipulation of the overtube within the body cavity. The method further comprises closing the seam of the segment of the overtube positioned over the endoscope mid shaft to form a longitudinally closed overtube and move the closed overtube over the endoscope shaft as guide within the body cavity and repeat the closing and moving till the overtube reaches the desired examination point, inflating the positioning ring to create a seal between the outer surface of the overtube and a body cavity proximal to the endoscope tip, wherein when inflated the positioning ring expanded asymmetrically around the overtube, inflating the at least one sealing band to create a seal between the internal surface of the overtube and endoscope shaft, passing the independently positionable occlusion catheter terminating in the asymmetrical occlusion balloon through a passageway along the overtube to enter the body cavity at the end of the overtube, manipulating the independently positionable occlusion catheter to a selected point within the body cavity distal to the endoscope tip, inflating the occlusion catheter balloon to create seal between the occlusion catheter balloon and the body cavity, and creating a sealed examination compartment between the positioning ring, the asymmetrical occlusion balloon and the sealing band surrounding the distal end of the endoscope shaft.

the endoscopic device includes an overtube including a longitudinal reclosable seam along an entire length of the overtube, an inner surface, an outer surface, a proximal end and a distal end, a positioning ring adjacent the distal end on the outer surface, at least one sealing band on the inner surface, an openable sheet having a first edge and opposed to a second edge, each one of the first edge and the second edge further including a closure, the first edge closure and the second edge closure coacting with one another to form an essentially cylindrical overtube, wherein the longitudinal reclosable seam includes adhesive and release sheet, spaced magnets, magnet strings, a zipper, which are carried by longitudinal edge portions along entire length of the longitudinal reclosable seam; at least one handle at the proximal end and on the outer surface for grasping and manipulation of the overtube within a body cavity.

The endoscopic device also includes an occlusion catheter located within a lumen of the overtube and terminating in an asymmetrical occlusion balloon, and an endoscope shaft located in the overtube and having a proximal end, a mid shaft, and a distal end, wherein the distal end terminates in an endoscope tip.

Moreover, the endoscopic device includes at least one flexible elongated sheet, sized to envelop a flexible endoscope or echoendoscope shaft and can envelop the endoscope or echoendoscope shaft without need to remove endoscope from the body; its opposed longitudinal edge portions can coact to form a flexible overtube receiving there within the endoscope or echoendoscope shaft.

The longitudinal edges of the endoscope accessory can be supplied with an adhesive along its entire length for coacting with the opposed edge portions to form a liquid tight seam along the entire length of the overtube. The adhesive can be covered by a release sheet that can be removed before adhering the two longitudinal end portions.

Alternative embodiments to using adhesive at the longitudinal edges of the endoscope accessory for creating the longitudinal seam can include using a plurality of spaced magnets or magnet strings on the longitudinal edge portions of the endoscope accessory sheet that are attracting the other magnets interspersed on the other longitudinal edge portion. To avoid activation of the magnets before placing the endoscope shaft within the overtube, at least one longitudinal edge portion can be supplied with a longitudinal magnet cover. Both longitudinal edge portions can be provided with a cover. The magnets can only coact with the opposed longitudinal edge portion magnets when the magnet covers are removed from the edge portion or portions.

The overtube can be provided with a handle on the external surface at the proximal end of the overtube for grasping and manipulation of the overtube within the body cavity. The handle is also the hub where a plurality of external inflation tubes and an irrigation/drainage port can connect to the overtube individually or in combination using a detachable multiple tube connection port. This can be used for connection of the overtube to inflation device, suction device, irrigation tube system or passage of therapeutic tools through the overtube.

The overtube can further include at least one inflatable positioning ring on external surface of the distal end portion of the flexible overtube for securing the position of the overtube within the body cavity. The inflated positioning ring can be asymmetric or eccentric in regard to the overtube. This allows a better sealing created by inflatable positioning ring within the body cavity and also improves the maneuverability of the endoscope tip within the body cavity.

The overtube can further include at least one positioning ring inflation tube in communication with the inflatable positioning ring for inflating or deflating the inflatable positioning ring.

The overtube can further include at least one inflatable sealing band on the internal surface of the overtube at the distal end portion of the overtube for creation of a seal around the endoscope shaft within the overtube. Alternatively, the inflatable sealing band can be replaced with an elastomeric sealing bead on the internal surface of the flexible overtube. The inflated sealing band can be eccentric to the overtube. This allows a better seal created by inflatable sealing band over endoscope. The inflated sealing band seals the distal end of the overtube around the endoscope to prevent the leakage of fluid and gas from the distal end of the overtube into the lumen of the overtube. Alternatively, the sealing band can be positioned on the internal surface of the overtube at the mid-portion, or proximal end portion of the overtube. Alternatively there could be more than one sealing band within the internal surface of the overtube.

The overtube can further include at least one sealing band inflation tube for inflating or deflating the inflatable sealing band/s.

The overtube can further include at least one catheter passageway, which defines a passageway for passing catheter or other accessories such as biopsy forceps and other endoscopic accessories from the overtube proximal end portion to the overtube distal end portion.

The endoscope accessory can also include at least one occlusion catheter carried by the overtube through the catheter passageway, having a free, independently positionable distal end portion that terminates in an inflatable occlusion balloon.

The occlusion catheter can include at least one occlusion balloon tube for inflating or deflating of the inflatable occlusion balloon and at least one a suction tube that terminates in a suction tip downstream of the occlusion balloon that facilitates injection of fluid or removal of secretions of body cavity distal to the occlusion balloon.

The endoscope accessory can also include at least one irrigation/drainage port. The irrigation/drainage port can be situated on the overtube handle and can include a closeable lid. The irrigation/drainage port can allow direct access to the lumen of the overtube. The irrigation/drainage port can be connected to irrigation/drainage tubes that can deliver water into or drain water out of the examination compartment in the gastrointestinal tract through the lumen of the overtube.

The overtube can further include at least one inflatable sealing band on the internal surface of the overtube at the proximal end portion of the overtube, proximal to the irrigation/drainage port for creation of a seal around the endoscope shaft within the overtube. Alternatively, the inflatable sealing band can be replaced with an elastomeric sealing bead on the internal surface of the flexible overtube. The inflated sealing band can be eccentric to the overtube. This allows a better seal created by inflatable sealing band over endoscope. The inflated sealing band seals the proximal end of the overtube around the endoscope to prevent the leakage of fluid and gas from the proximal end of the overtube. Therefore, the fluid and gas can be purged into or drained from the lumen of the overtube through the irrigation/drainage port, while the endoscope is still within the overtube without leakage of the fluid or gas from the proximal end of the overtube. The overtube can further include at least one sealing band inflation tube for inflating or deflating the proximal inflatable sealing band.

The overtube can further include at least one fluid/insufflation conduit that defines a passageway for inflating or suctioning fluid or air within the examination compartment within the body cavity at the distal end of the overtube.

The overtube can further include at least one accessory channel that defines a passageway for passing accessory tools from the proximal end of the overtube into the examination compartment within the body cavity at the distal end of the overtube.

The overtube can further include at least a suction conduit connected to a suction port situated on the external surface of the overtube between the inflatable positioning ring and the proximal end portion of the overtube. The suction port can be used to remove the secretions that accumulate proximal to the inflatable positioning ring in the body cavity.

The overtube can further include at least a flushing port situated on the external surface of the overtube between the inflatable positioning ring and the proximal end portion of the overtube. The flushing port can be used to inject fluid or gas to flush the body cavity proximal to the inflatable positioning ring in the body cavity.

The overtube can further include fenestration holes connecting the external surface of the overtube to the internal surface of the overtube, between the inflatable positioning ring and the proximal end portion of the overtube. The fenestration holes can allow a passive passage of fluid, secretion and gas from the lumen of gastrointestinal tract proximal to the inflatable positioning ring to the lumen of the overtube for drainage of the body cavity.

The overtube can further include at least one quick connect fitting. The quick connect fitting allows a detachable coupling of multiple tubes at the proximal end portion of the overtube into an umbilical extension tube. The umbilical extension tube has one quick connect fitting on each end and serves as an extension tubing to connect the overtube to inflation, irrigation, insufflation or suction devices. The male-female interface of the quick connect fitting allows a detachable connection of multiple ports and tubes with one locking action. Example of the ports and tubes that can be detachably attached through the quick connect fitting can include but not limited to inflation tube for positioning ring, inflation tube for sealing band/s, inflation tube for occlusion balloon, insufflation port for insufflation with gas, irrigation tube for flushing port, suction conduits and fluid/insufflation conduit.

The overtube can further include at least one occlusion balloon quick connect fitting at the handle at the proximal end portion of the overtube. The male-female interface of the occlusion balloon quick connect fitting allows a detachable coupling of the proximal end of the occlusion balloon tube to be connected overtube handle. The interface of the occlusion balloon quick connect fitting on the overtube handle allows the occlusion balloon to be connected to the quick connect fitting that eventually connects to the umbilical extension tube.

The overtube can further supplied with an automated control system for automated control of inflation, insufflation, irrigating and suctioning through the over tube. The automated control system can control the inflation of the positioning ring, the sealing band/s or the occlusion balloon, insufflation of the compartment, injection or irrigating fluid into the irrigation/drainage port, irrigation conduit of flushing port and suctioning of the suction conduit/s. The automated control system can inflate and maintain each individual balloon pressure at an assigned set point, insufflate and maintain the compartment pressure at an assigned set point, inject fluid into the assigned port and apply suction pressure to an assigned conduit. The activation and set points of the functions are adjusted through knobs or digital displays. The automated control system includes at least one quick connect fitting. The quick connect fitting allows a detachable coupling of multiple tubes to the umbilical extension tube. As mentioned above, the umbilical extension tube is connected from the other end to the overtube proximal end portion through another quick connect fitting. The male-female interface of the quick connect fitting allows a detachable connection of multiple ports and tubes with one locking action.

Through the umbilical extension tube, the plurality of the overtube's ports, tubes and conduit are connected to the corresponding inflation, insufflation, irrigation, and or suctioning tubes on the automated control system.

The automated control system has a power switch, multiple knobs, buttons and digital display for monitoring, adjusting and controlling the various function of the overtube during the procedure based on the application.

The longitudinal edge portions of the overtube can be supplied with plurality of spaced magnets covered by a magnet cover comprised of a slit sleeve and the like. The magnets on the longitudinal edge portions are able to coact upon removal of the magnet cover. The magnet pieces on one edge portion are interspersed with the spaced magnets on the other longitudinal edge portion to form the seam.

Alternatively, the longitudinal edge portions of the overtube can be supplied with linear string of magnets. The magnet strings on each side of the opposed edge can be covered by a magnet cover comprised of a slit sleeve and the like. The magnets on the longitudinal edge portions are able to coact upon removal of the magnet cover. In this form, the magnet beads on one edge portion are not interspersed and coact directly with the opposed longitudinal edge portion to form the seam.

Magnets beads can be positioned directly at the edge portion of the overtube or alternatively, the magnet beads can be placed in a silicon or plastic tube to form a magnet string and the tube containing magnet string is attached to the longitudinal edge portions of the opposed edges of the longitudinal seam of the overtube. The tube containing the magnet beads cab be attached just at the edge, under or over the edge on the opposed side of the seam.

Alternatively, the seam can be created by self fusing silicon tape, other interlocking mechanisms such as tongue and groove, complementary edges, hook and loop, zip-lock-type fastener, adhesive tapes, adhesive straps, self-fusing silicon tapes and straps and the like or a combination of these mechanisms, particularly the combination of self fusing silicon tape and magnet beads.

In use, the endoscope accessory of the claimed invention is a flexible, elongated sheet that envelops the endoscope or echoendoscope shaft while the endoscope shaft is still within the body cavity without the need to remove the endoscope or pre-position the overtube over the endoscope shaft prior to the endoscope insertion within the body cavity. However, as those skilled in the arts can understand, the device could be placed prior to endoscope insertion.

After enveloping or surrounding the endoscope shaft by the sheet, the opposing longitudinal edge portions can be joined to form an overtube by creating a longitudinal seam along the entire length of the overtube. The opposed longitudinal edge portions of the sheet can be supplied with adhesive, covered by a release sheet. To form the overtube, the release sheet is removed and the opposed longitudinal edge portions coact using adhesive to form a liquid tight seam.

After closure of the overtube seam along the overtube's length, the endoscope shaft is enveloped within the overtube, the handle of the overtube is grasped and the overtube is pushed into the body cavity of a patient with the guide of the endoscope shaft to be placed at the desired location, just proximal to the tip of the endoscope.

The inflatable positioning ring is inflated to secure the position of the overtube distal end portion within the body cavity and create a seal between the overtube and body cavity.

The inflatable sealing band can be inflated to secure the position of the endoscope within the overtube and create a seal around the endoscope shaft within the overtube. The endoscope can be moved independent of the overtube while the sealing band is inflated keeping the seal. The endoscope can be replaced when the inflatable sealing band is not inflated, if desired, with another endoscope while the overtube stays in its position within the body cavity.

The occlusion balloon catheter is passed through the catheter passageway to be placed independently beyond the distal tip of the overtube and endoscope tip. After the inflatable occlusion balloon exits the catheter passageway at the distal tip of the overtube, it is placed at the desired location, distal to the distal tip of the endoscope. Then, the inflatable occlusion balloon is inflated. This secures the position of the occlusion balloon within the body cavity and also seals the body cavity from passage of gas or liquid.

Inflation of the occlusion balloon creates an examination compartment, which is defined by the inflated positioning ring, inflated sealing band and the inflated occlusion balloon around the tip for the endoscope at the distal end of the overtube.

The examination compartment can be filled with air, or water, depending on applications. In addition the examination compartment can be thoroughly lavaged using the irrigation tubes connected to irrigation/drainage port or the proximal overtube opening. During the irrigation process the inflated balloons prevent escape of air or water from the examination compartment. During the irrigation process, the endoscope tip can remain at the examination compartment, be pulled back to the proximal end portion of the overtube or be completely removed. In the latter case the proximal sealing band can be inflated to seal the overtube completely or the proximal opening of the overtube can be closed shut using a proximal overtube cap. Throughout the procedure, pressure within the examination compartment can be maintained and monitored using the fluid/insufflation conduits.

The examination compartment can be made smaller or larger by changing the position of the occlusion balloon by pushing or pulling the positioning ring catheter without need for deflation of the positioning ring.

The examination compartment can be moved along the body cavity, by pushing or pulling the entire overtube without need for deflation of the occlusion balloon, positioning ring or sealing band.

When the compartment is moved along the body cavity, it maintains its pressure and its content of air or water based on the application. This allows the endoscope to examine an extended part of the gastrointestinal tract as the location of the compartment glides over the intestinal lumen. At the preference of the user the movement can be stopped or reversed.

When the compartment is moved along the body cavity while the balloons are inflated, the movement of the inflated balloons along the gastrointestinal lumen creates a squeegee action and wipes the intestinal wall off of fluid secretion and residuals away from the moving compartment. This allows physical cleaning and wiping of the intestinal lumen before examination by the endoscope. This is particularly important when the inflated positioning ring wipes the intestinal wall off of fluid and residuals when the overtube is pulled out of the body cavity.

When the compartment is moved along the body cavity while the balloons are inflated, the squeegee action of the balloons wipes the intestinal wall off of fluid secretion and residuals away from the moving compartment. During this movement, the flushing port situated on the external surface of the overtube between the inflatable positioning ring and the proximal end portion of the overtube are used to inject fluid to flush the body cavity proximal to the inflatable positioning ring. This enhances the cleaning squeegee action of the inflated positioning ring.

When the compartment is moved along the body cavity while the balloons are inflated, the squeegee action of the balloons wipes the intestinal wall off of fluid secretion and residuals away from the moving compartment. The injected fluid through flushing port and the luminal fluid and residuals that are propelled during the cleaning squeegee action of the inflated positioning ring are accumulated proximal to the inflatable positioning ring over the external surface of the overtube. The fenestration holes connecting the external surface of the overtube to the internal surface of the overtube between the inflatable positioning ring and the proximal end portion of the overtube allow a passive passage of fluid, secretion and gas from the lumen of gastrointestinal tract proximal to the inflated positioning ring to the lumen of the overtube. The fluid and gas, eventually drains from the overtube lumen through the irrigation/drainage port on the overtube handle. The sealing balloon at the proximal end portion of the overtube prevents leakage of the fluid from the proximal end of the over tube.

The examination compartment can be used as a sealed compartment for possible surgeries or access to spaces outside of gastrointestinal tract. In that case, after inflating the positioning ring and occlusion balloon, the endoscope can be removed and other surgical device/s is/are placed within the compartment. The sealing band is inflated or remains deflated based on the user preference. The surgical device can create a puncture in the wall of the gastrointestinal tract inside the compartment to access the space beyond GI tract lumen. The device can perform possible surgical intervention beyond the gastrointestinal tract while the compartment prevents the passage of air and fluid from other part of the gastrointestinal tract to the surgical site inside the compartment. The surgical devices can be used for examination of peritoneum or perform intraperitoneal surgeries. After termination of the surgical procedure, the surgical device can be removed after sealing band deflation. Then, the opening in the gastrointestinal tract can be closed by the appropriate device or technique including using sutures, clips, staples or the same. Then the endoscope can be reintroduced into the compartment for further examination.

The occlusion balloon, positioning ring and sealing band can be deflated and re-inflated independent of each other or together as determined by the user.

After termination of the examination, the positioning ring, sealing band and occlusion balloon are all deflated and the overtube is removed independent of, or together with, the endoscope.

IV. BRIEF DESCRIPTION OF THE DRAWINGS

Figure 10A:
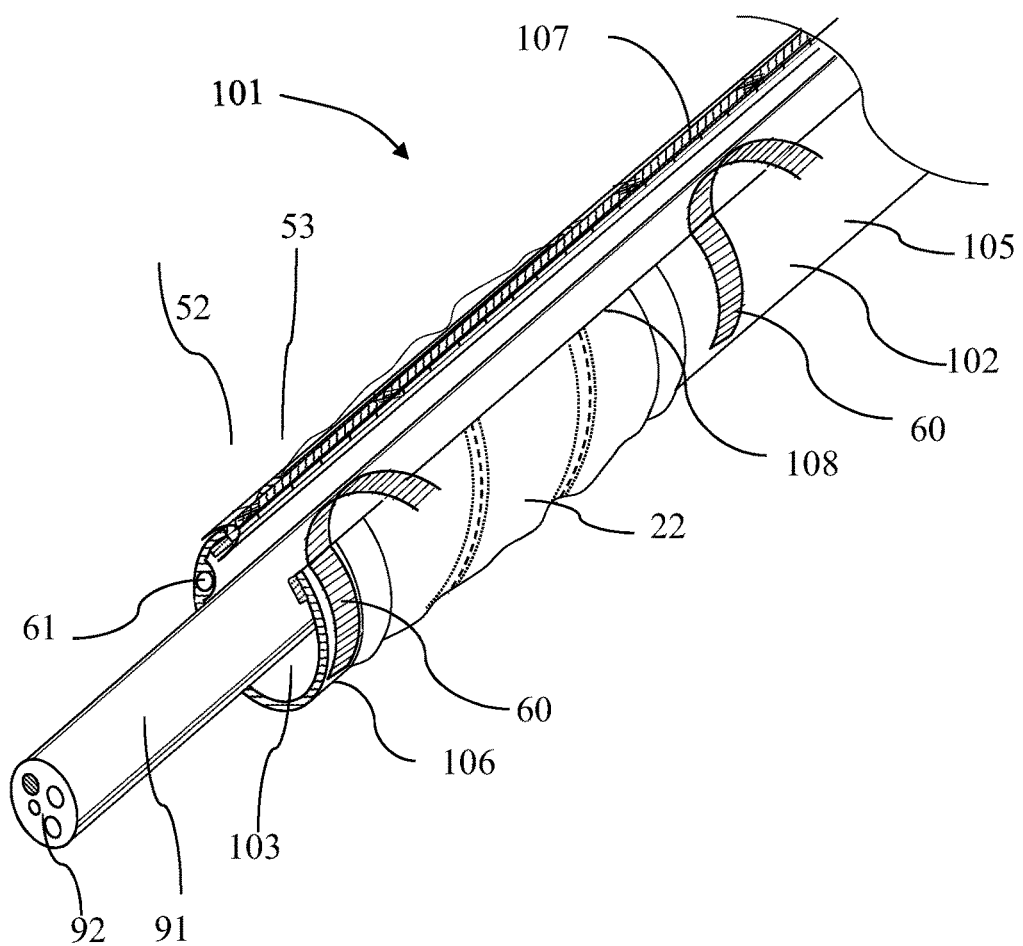
FIG. 10A is a partial schematic illustration of the endoscope accessory showing magnet strings under the longitudinal edge of the tube and one magnet cover at the longitudinal edge portions and adhesive tape belts for closing the seam after removing the release sheets to attach over the opposing edge portions.
Figure 10B:
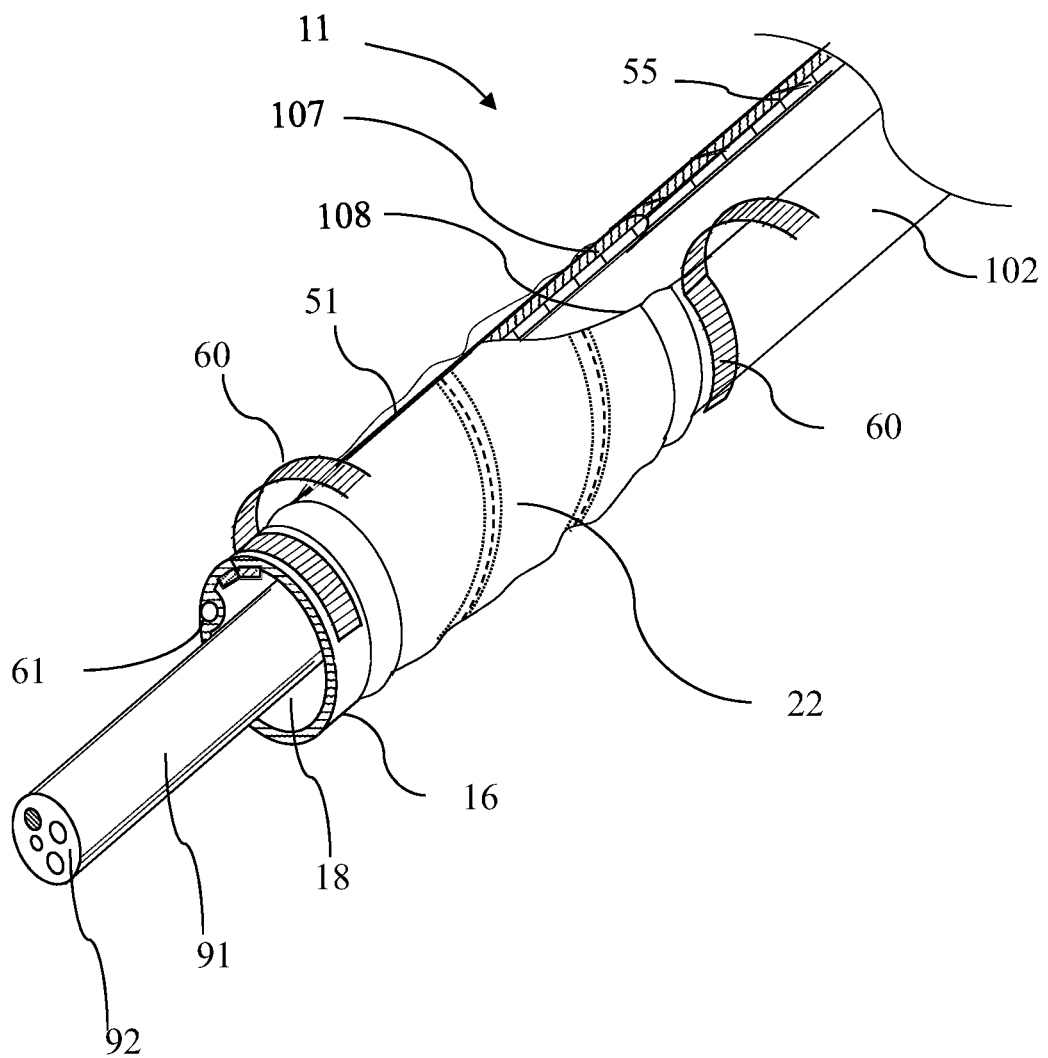

FIG. 10B is a partial schematic illustration of the endoscope accessory showing magnet strings under the longitudinal edge and one magnet cover at the longitudinal edge portions after placement of the endoscope shaft and partial closure of the longitudinal seam by magnets showing the adhesive tape belts for closing the seam after removing the release sheets to attach over the opposing edge portions after closure of seam.

Figure 11A:
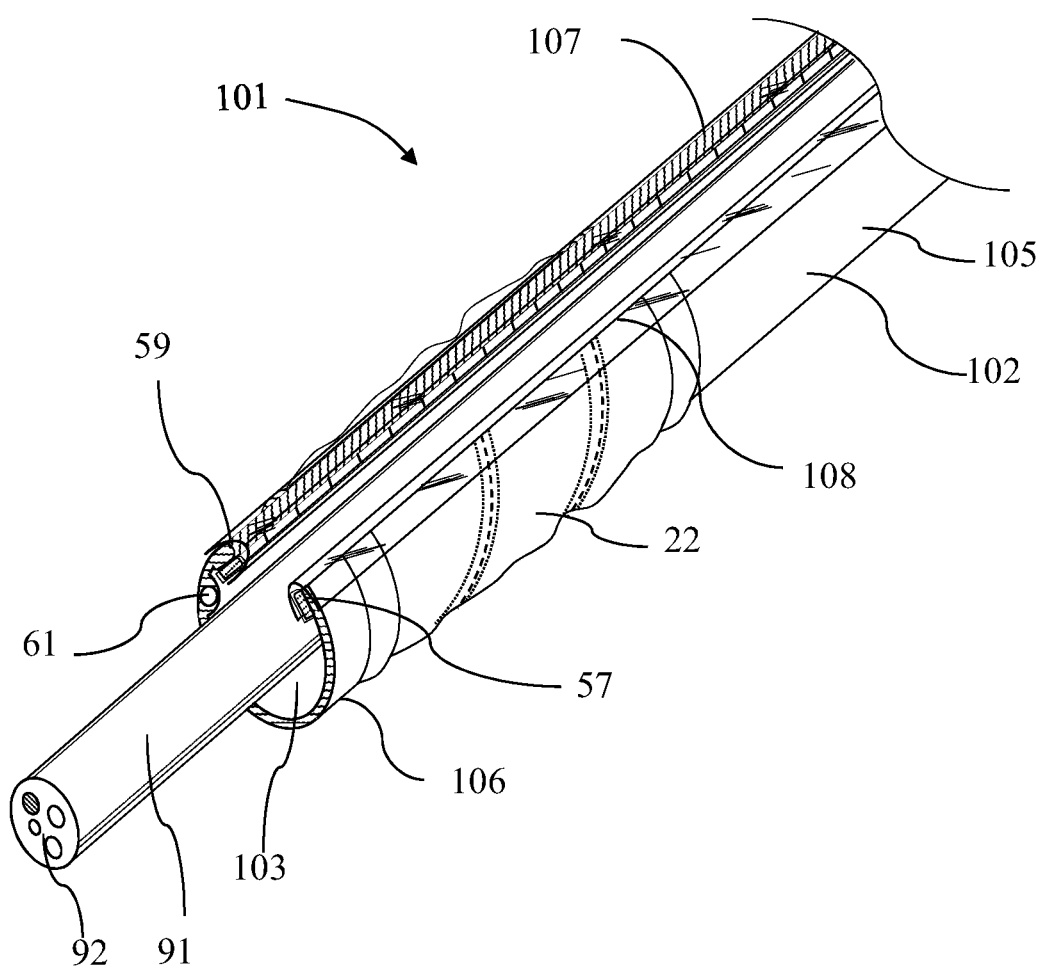

FIG. 11A is a partial schematic illustration of the endoscope accessory showing magnet string flap under one longitudinal edge of the tube and magnet string under the other longitudinal edge of the tube and magnet covers at the longitudinal edge portions holding up the magnet flap on one side and cover the magnet string on the other side.

Figure 11B:
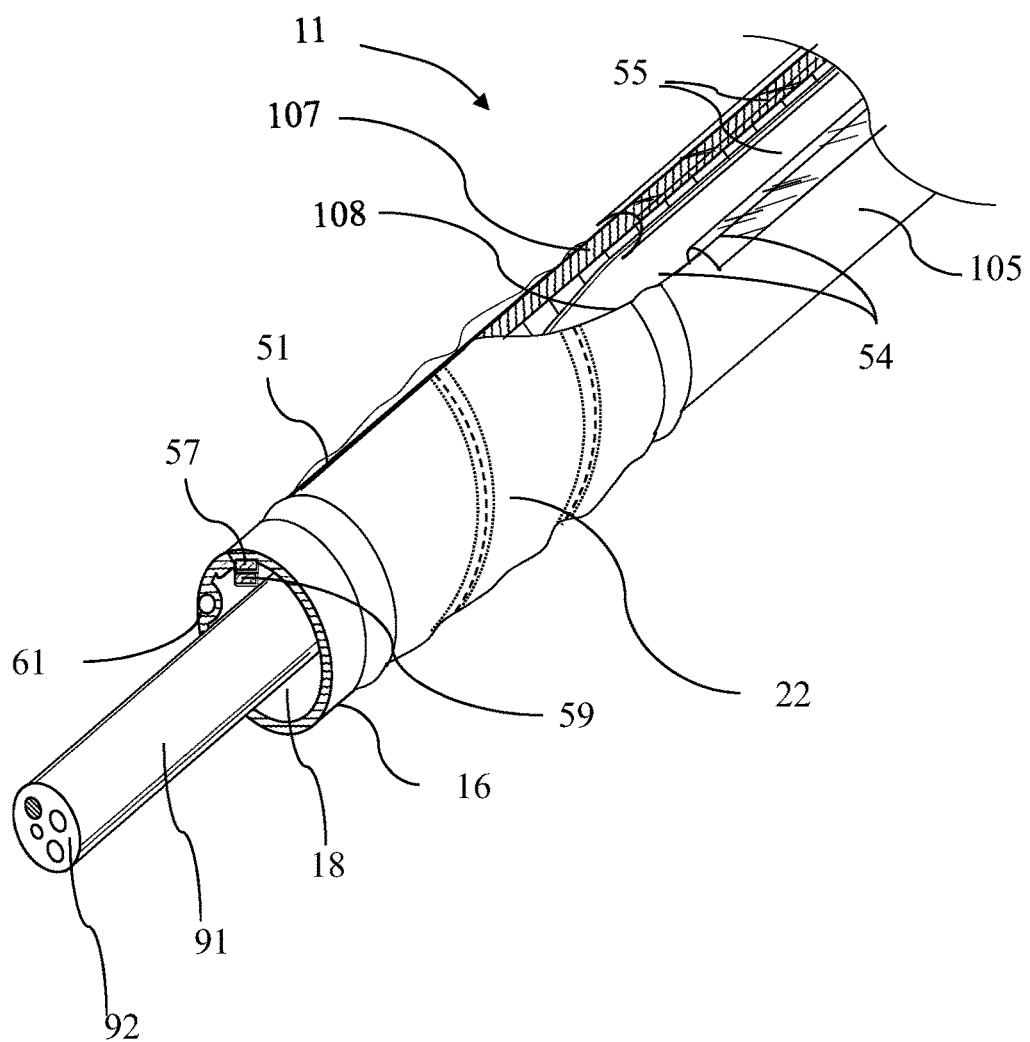

FIG. 11B is a partial schematic illustration of the endoscope accessory showing one magnet string flap at the longitudinal edge of the tube on one side while its magnet cover is being partially removed by longitudinally retracting the magnet cover, releasing the magnet string flap, allowing the magnet string flap to swing toward the opposing edge portion. The other opposing edge is supplied with magnet string under the longitudinal edge of the tube and a magnet cover at the longitudinal edge portions vovering the magnet string to prevent attraction from the opposing edge magnets.

Figure 12A:
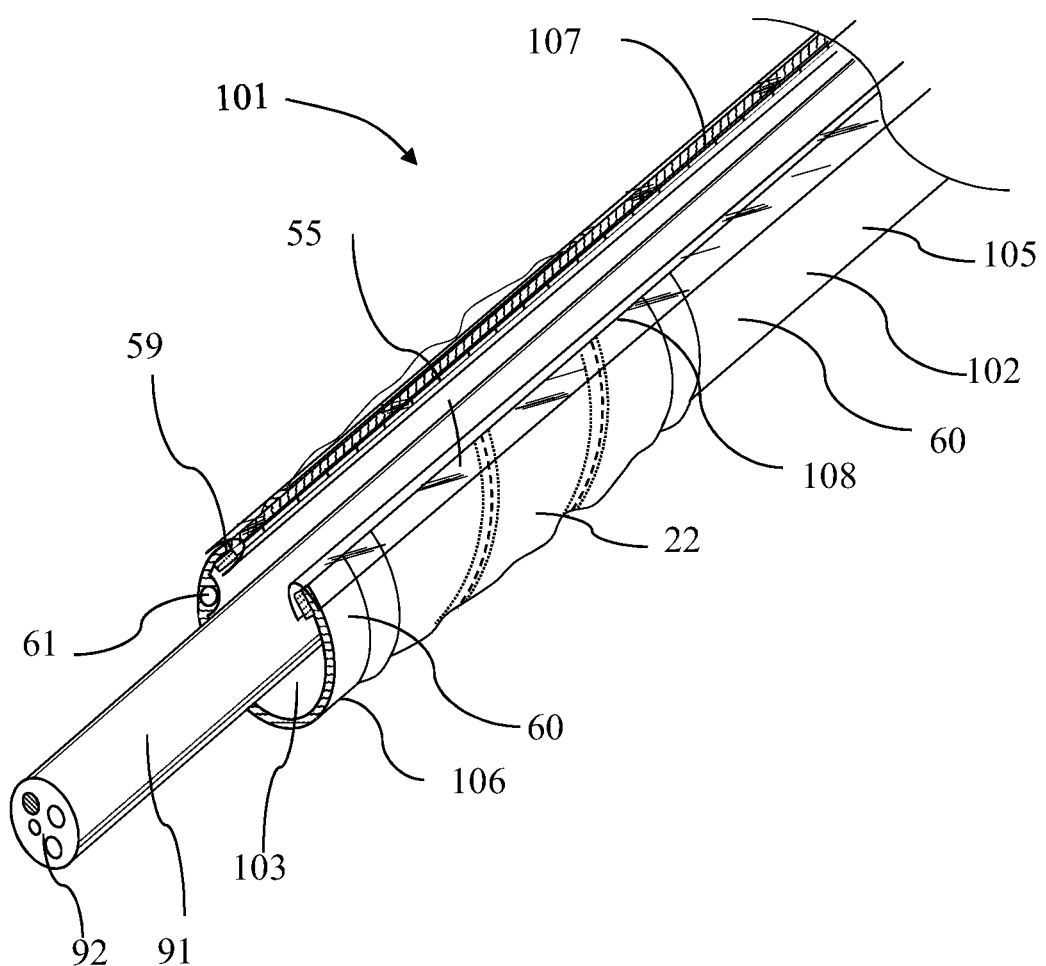

FIG. 12A is a partial schematic illustration of the endoscope accessory showing magnet string flaps under the longitudinal edge of the tube and magnet covers at the longitudinal edge portions holding up the magnet flaps.

Figure 12B:
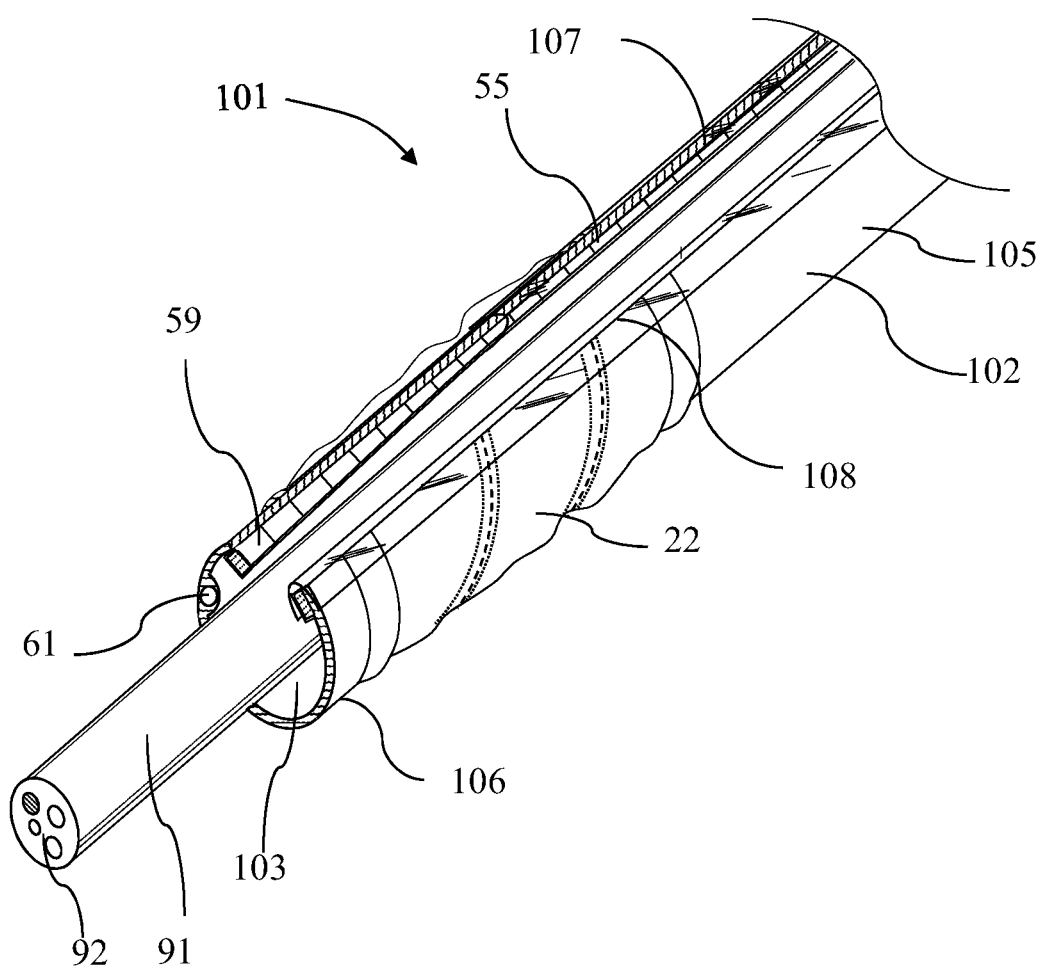

FIG. 12B is a partial schematic illustration of the endoscope accessory showing one magnet string flap at the longitudinal edge of the tube on one side while its magnet cover is being partially removed by longitudinally retracting the magnet cover, releasing the magnet string flap, allowing the magnet string flap to swing toward the opposing edge portion. The other opposing edge is supplied with another magnet string flap under the longitudinal edge of the tube and its magnet cover at the longitudinal edge portions holding up the magnet flap under the longitudinal edge of the tube to prevent attraction from the opposing edge magnets.

Figure 12C:
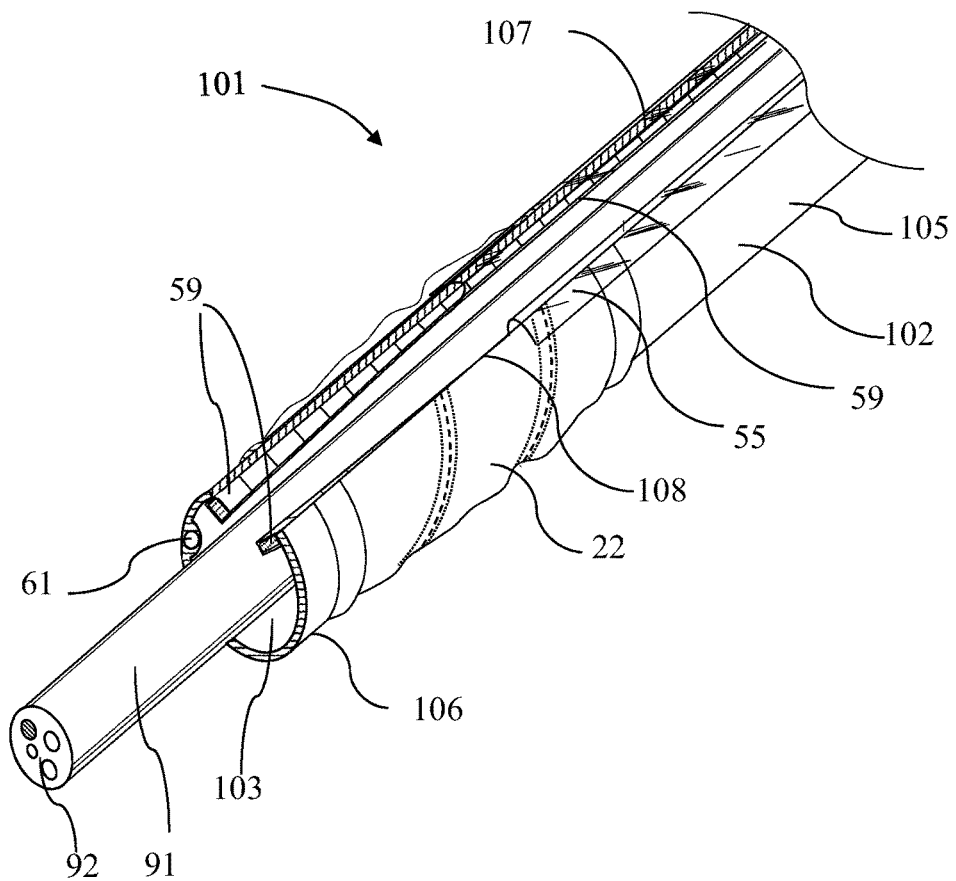

FIG. 12C is a partial schematic illustration of the endoscope accessory showing magnet string flaps at the longitudinal edge of the tube on the both sides while the magnet covers are being partially removed by longitudinally retracting the magnet covers, releasing the magnet string flaps, allowing the magnet string flaps to swing toward the opposing edge portions. The released magnet string flaps are allowed to attract the opposing edge magnet string flap.

Figure 12D:
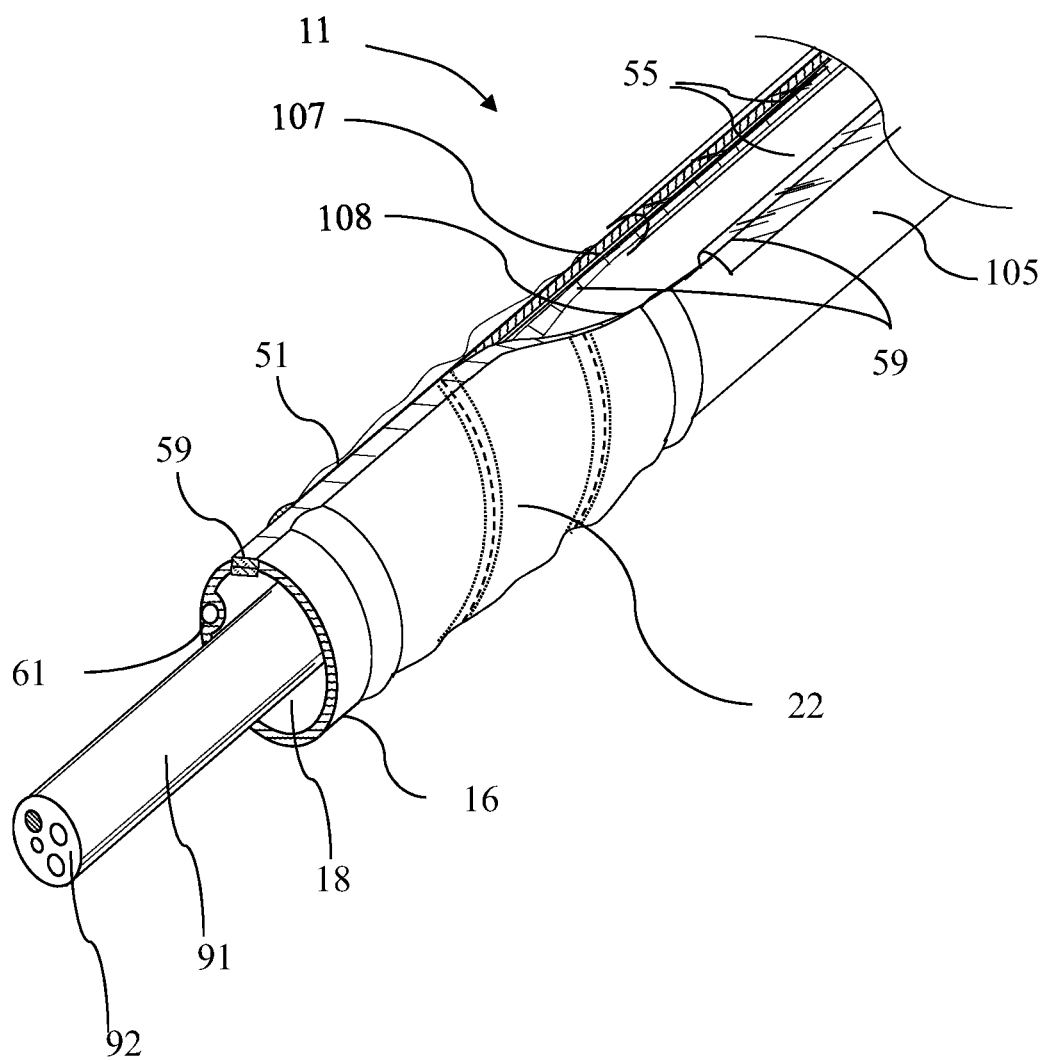

FIG. 12D is a partial schematic illustration of the endoscope accessory showing magnet string flaps at the longitudinal edge of the tube on both sides while the magnet covers are being partially removed by longitudinally retracting the magnet covers, releasing the magnet string flaps, allowing the magnet string flaps to swing toward the opposing edge portions after placement of the endoscope shaft. The released magnet string flaps are allowed to attract the opposing edge magnet string flap that results in partial closure of the longitudinal seam.

Figure 13A:
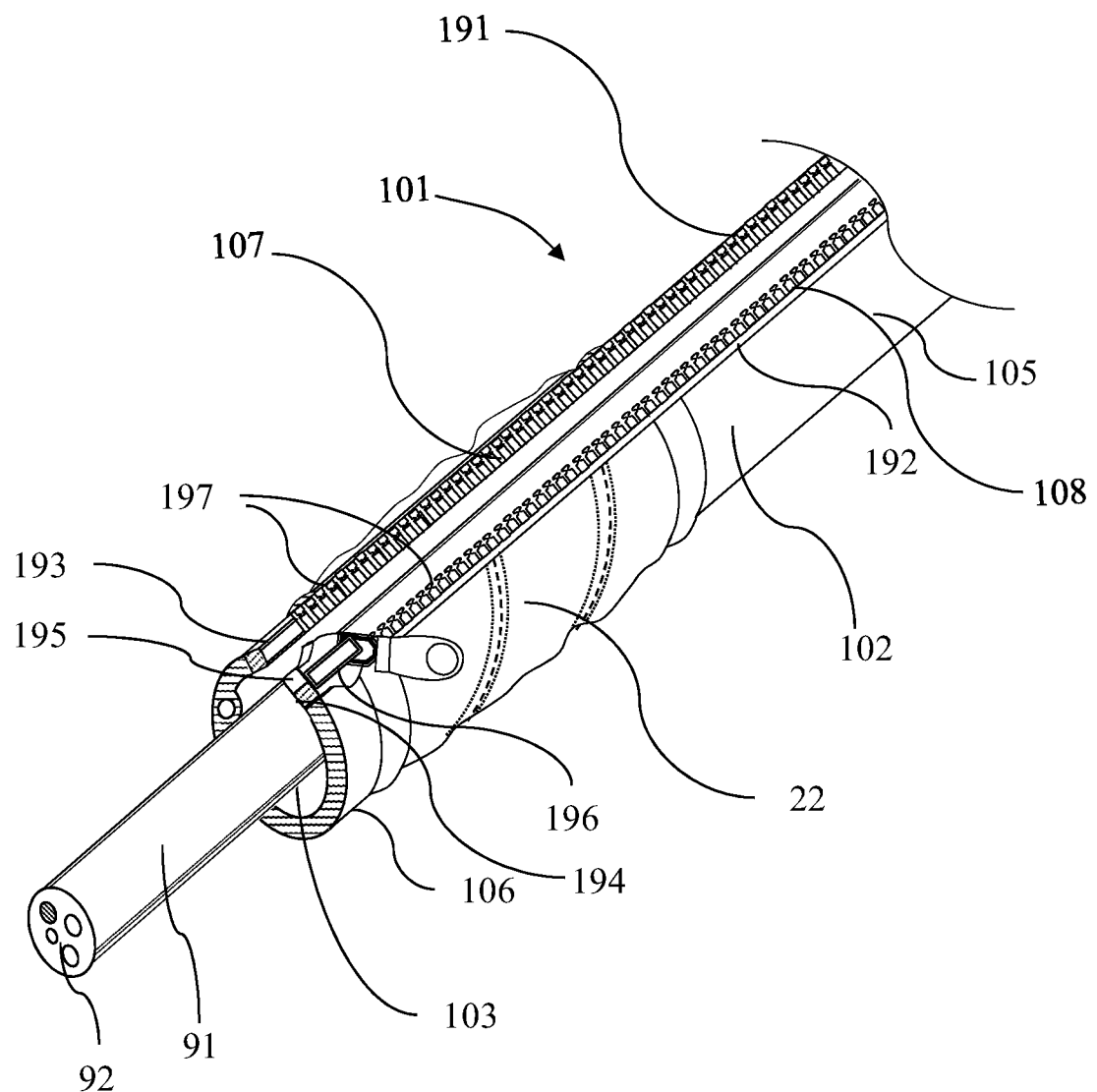

FIG. 13A is a partial schematic illustration of the endoscope accessory showing an open ended zipper at the longitudinal edge of the tube in a fully opened status.

Figure 13B:
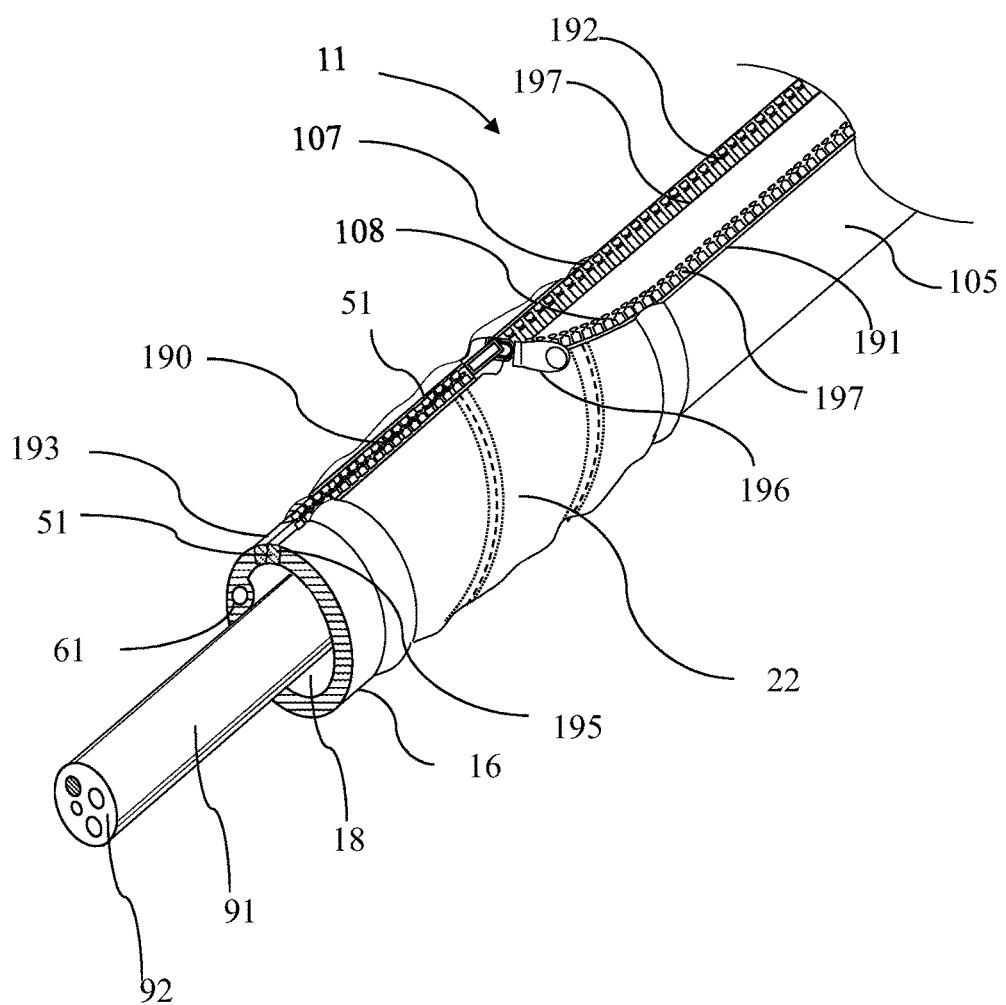

FIG. 13B is a partial schematic illustration of the endoscope accessory showing an open ended zipper at the longitudinal edge of the tube after the zipper insert pin from one edge is placed in the zipper retaining box from the opposing edge and slider is move to engage the zipper teeth that results in partial closure of the longitudinal seam.

Figure 14A:
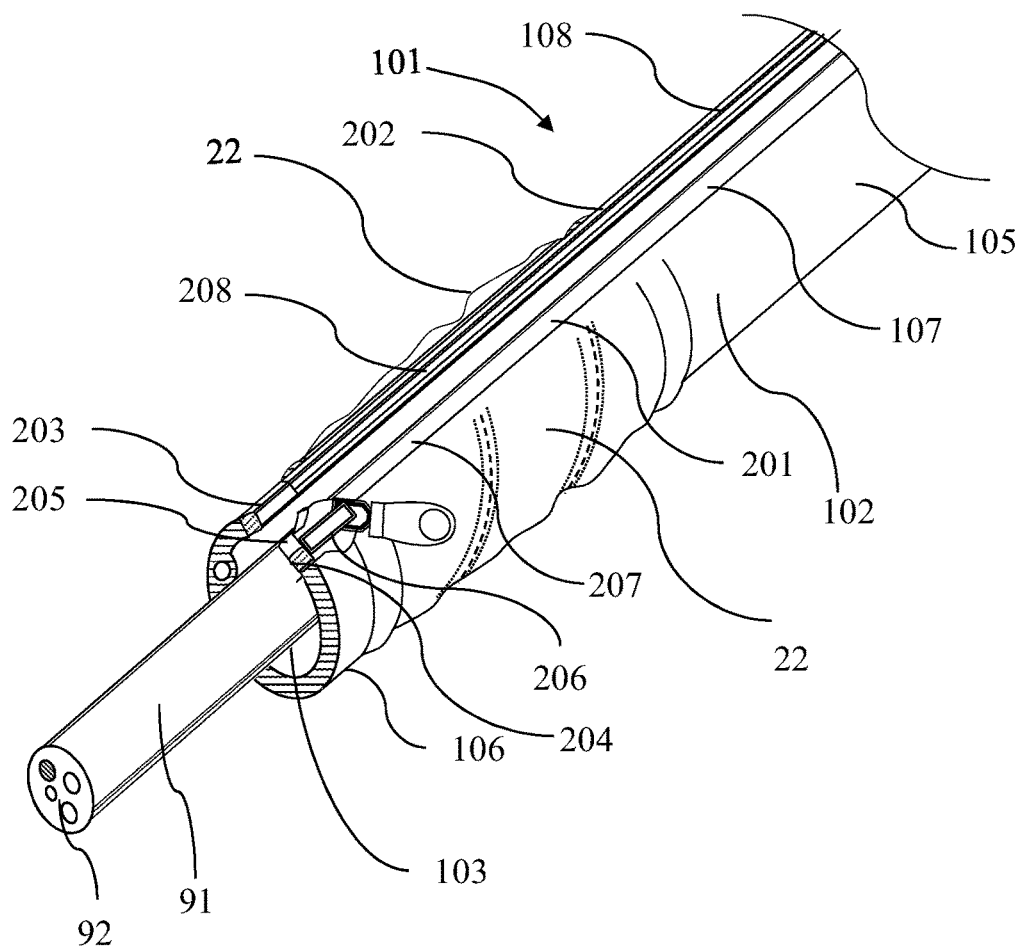

FIG. 14A is a partial schematic illustration of the endoscope accessory showing an open ended toothless zipper at the longitudinal edge of the tube in a fully opened status.

Figure 14B:
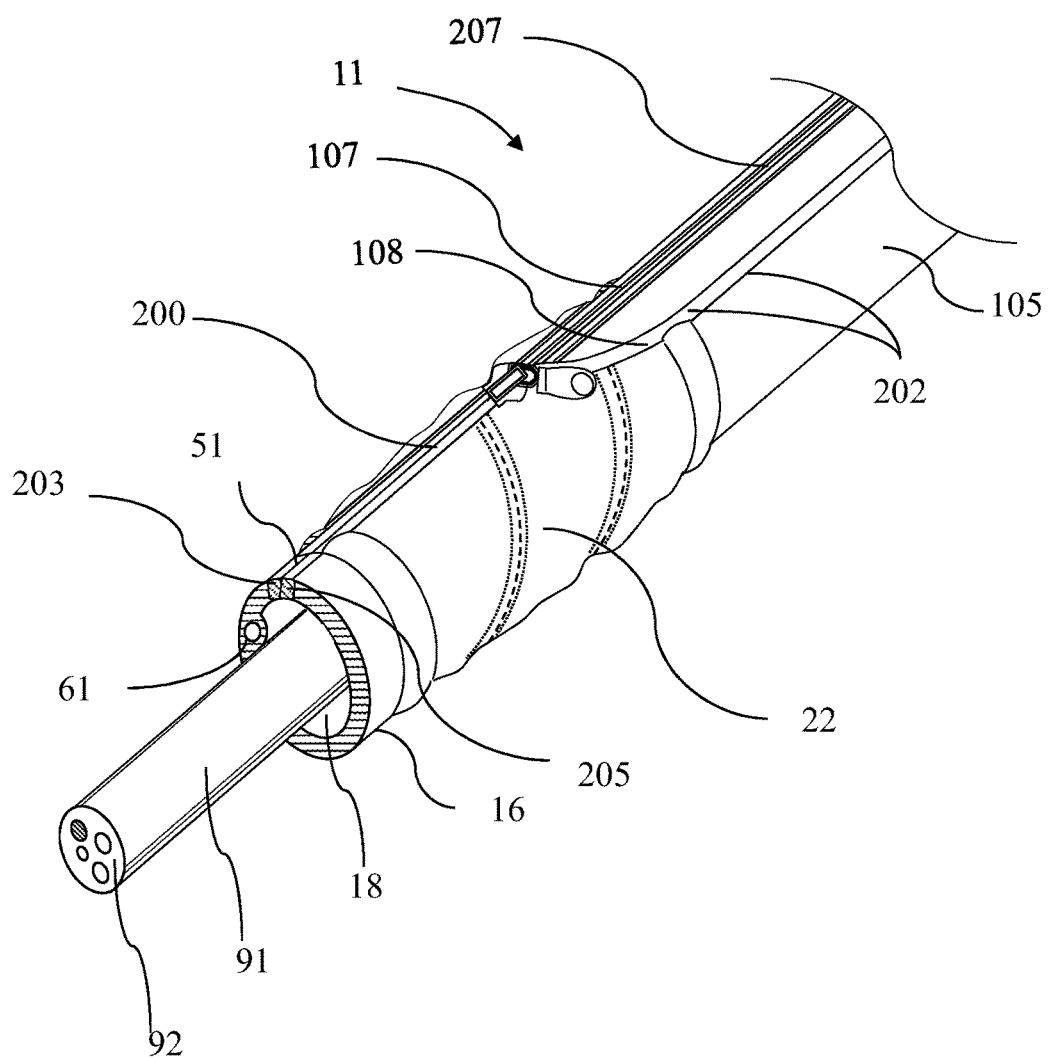

FIG. 14B is a partial schematic illustration of the endoscope accessory showing an open ended toothless zipper at the longitudinal edge of the tube after the zipper insert pin from one edge is placed in the zipper retaining box from the opposing edge and slider is moved to engage the zipper locking edges that results in partial closure of the longitudinal seam.

Figure 15:
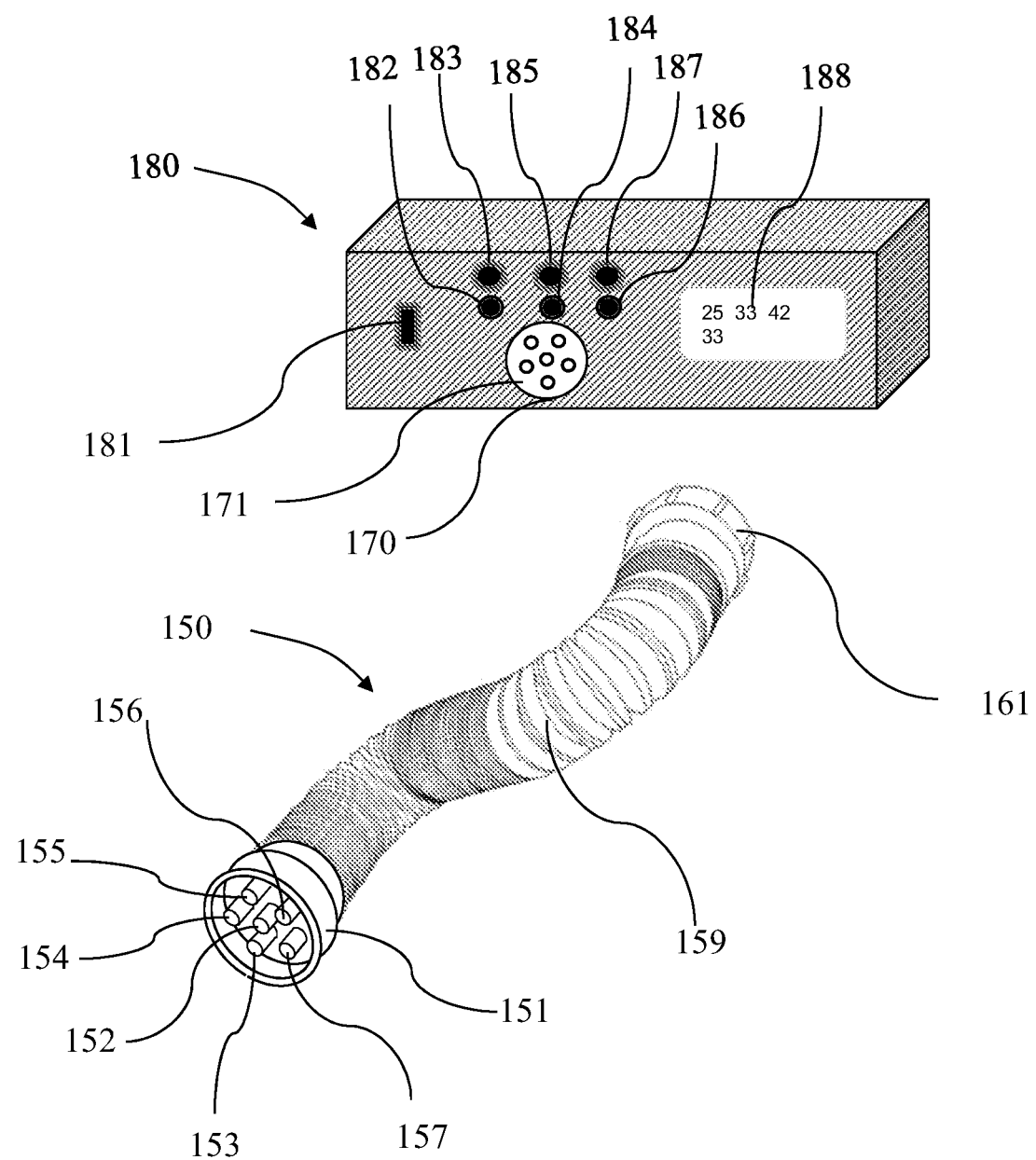

FIG. 15 is a schematic illustration of the umbilical extension tube and the automated control system.

Figure 16A:
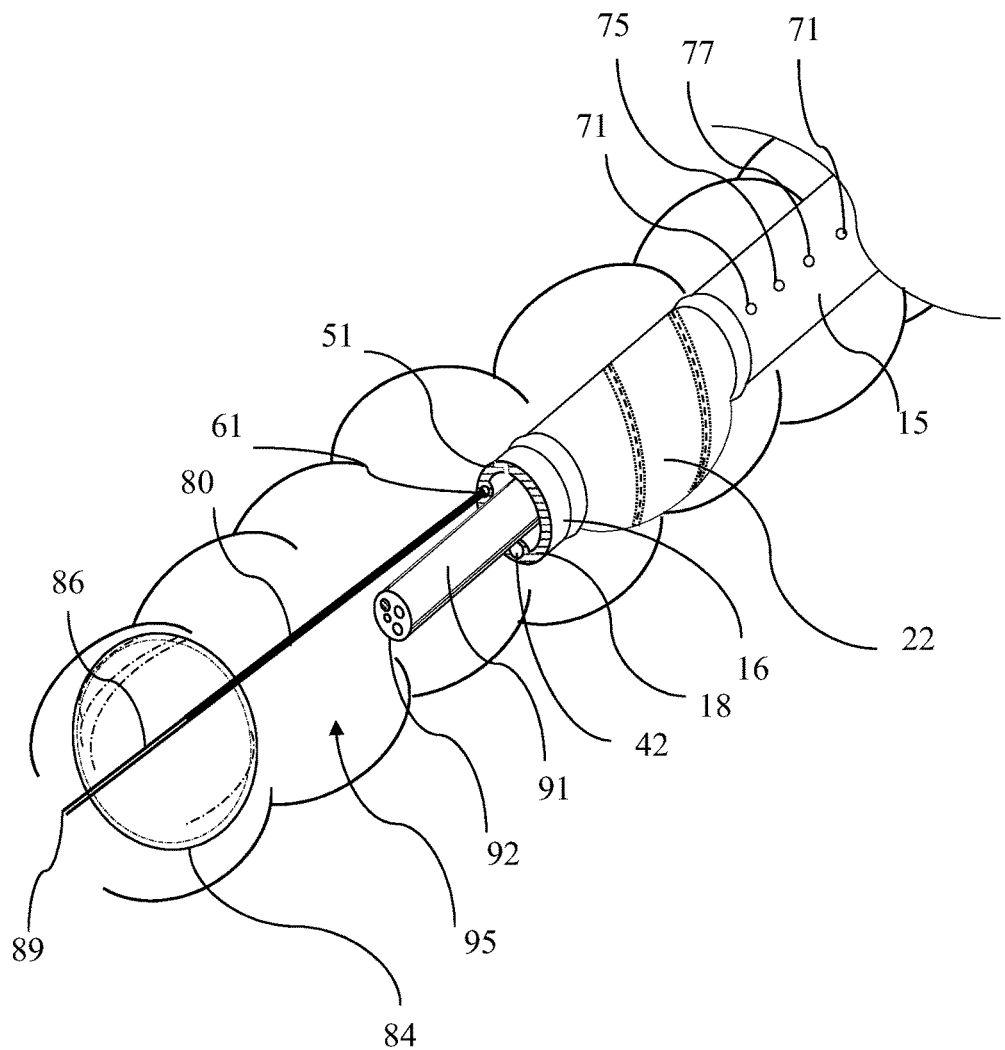

FIG. 16A is a schematic illustration of the endoscope accessory creating an examination compartment within the lower gastrointestinal tract and access beyond the GI tract, and in FIG. 16A endoscope is the center of the compartment.

Figure 16B:
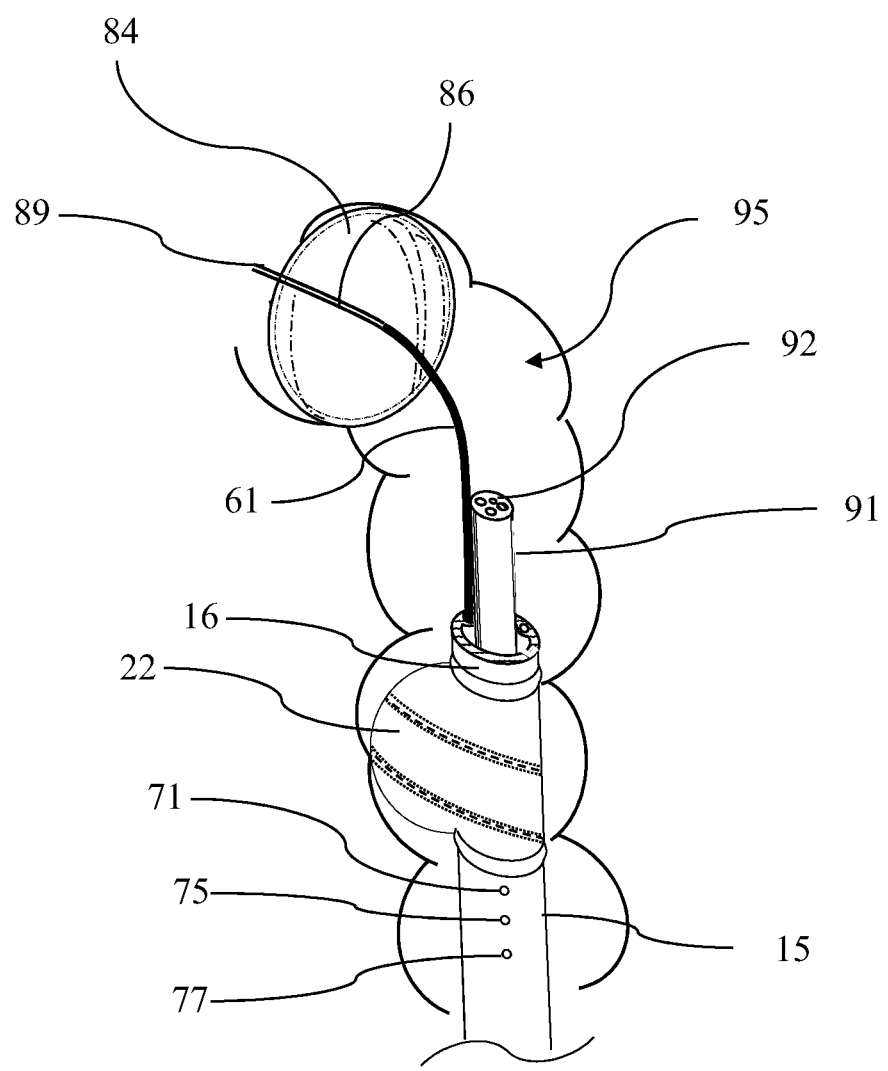

FIG. 16B endoscope is the center of the compartment at a bend in the colon.

Figure 16C:
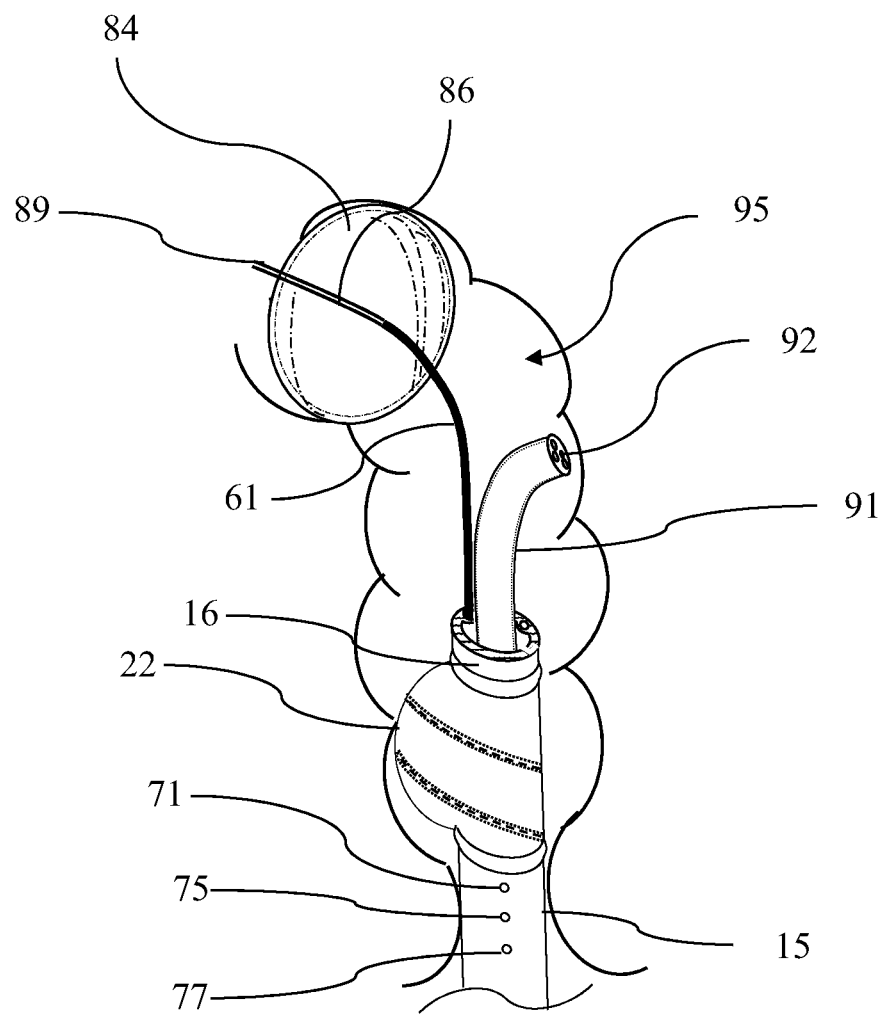

FIG. 16C endoscope is facing the GI tract wall.

Figure 16D:
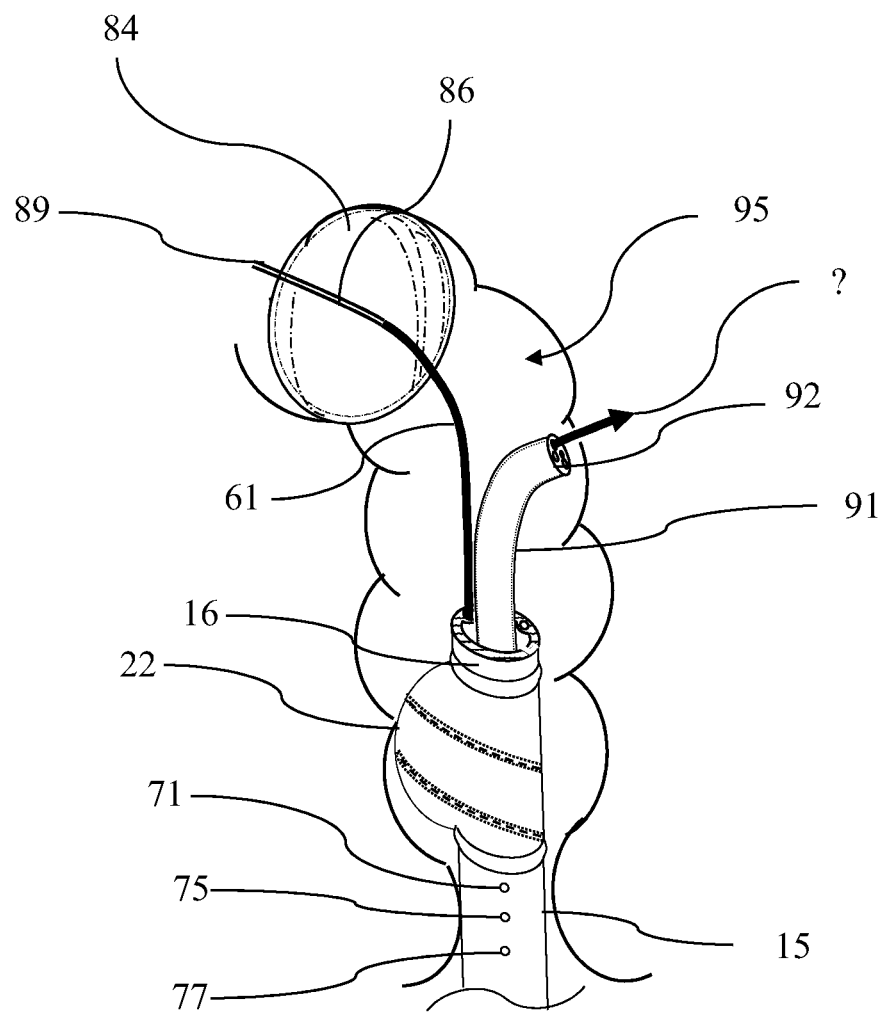

FIG. 16D endoscope is creating a passage in the GI tract wall.

Figure 16E:
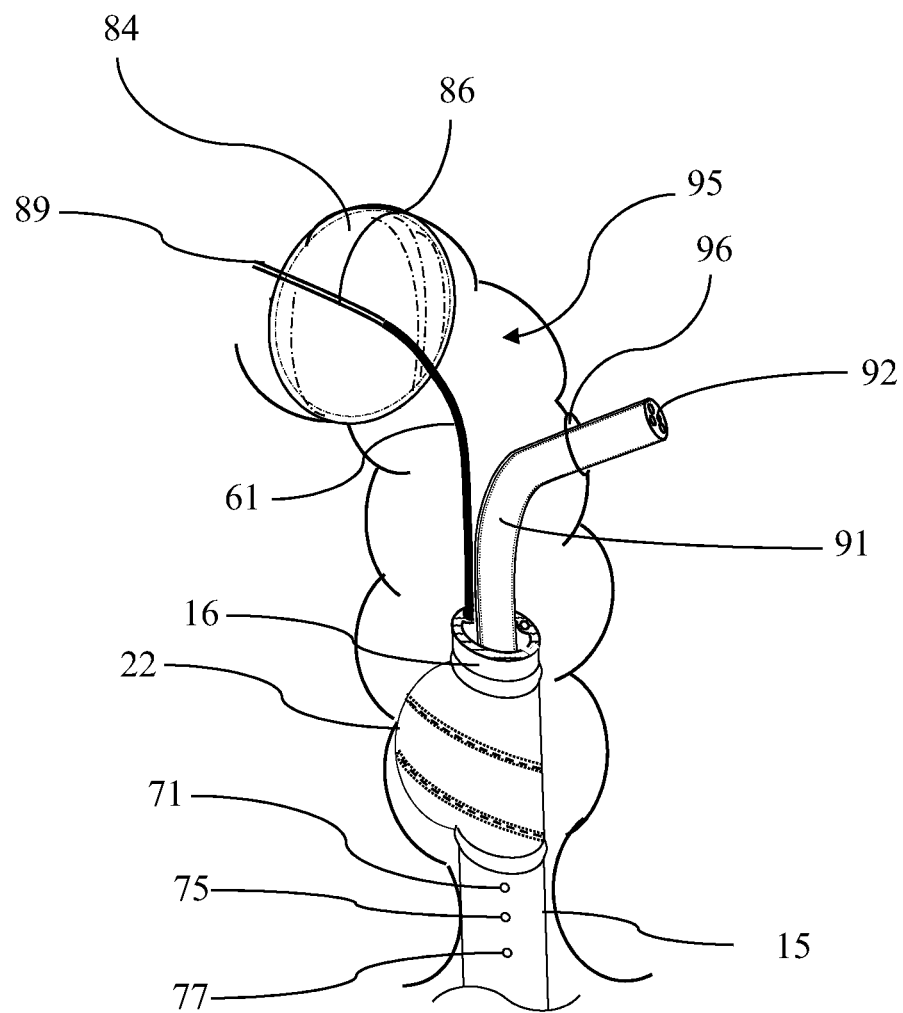

FIG. 16E passes beyond the GI tract wall into peritoneal cavity.

Figure 17A:
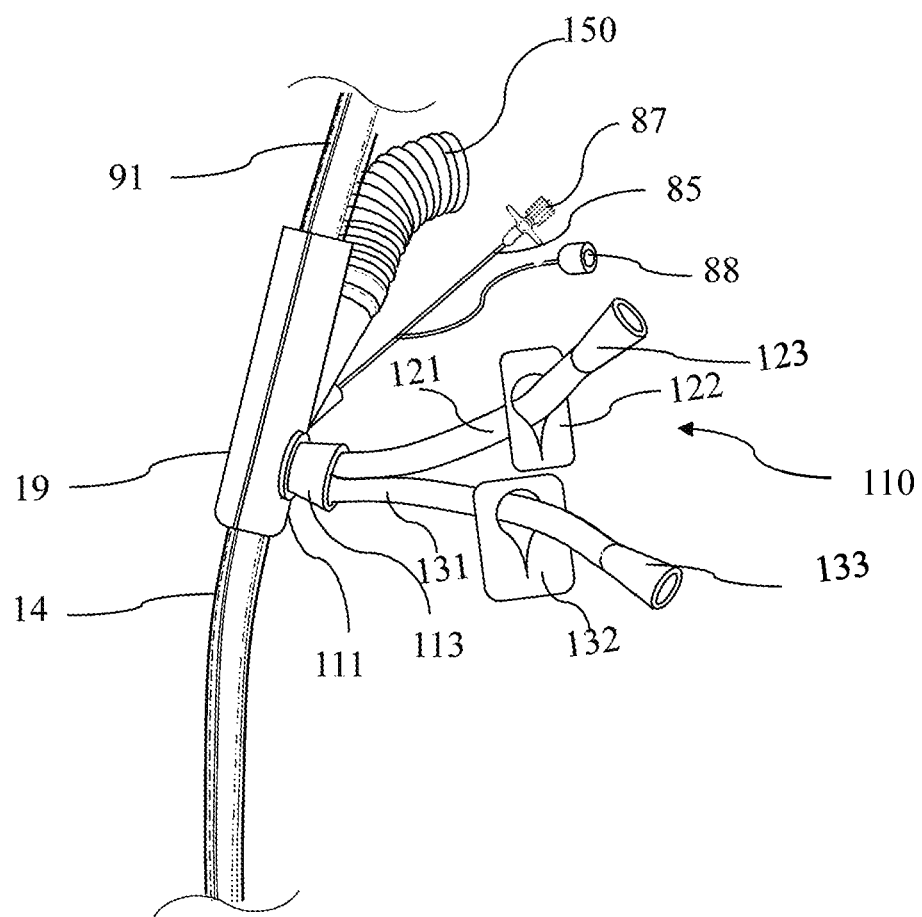

FIG. 17A is a perspective view of an alternate embodiment of the present invention depicting endoscope accessory with endoscope in the overtube and the irrigation/drainage port is uncapped and is connected to an irrigation/drainage tube connector.

Figure 17B:
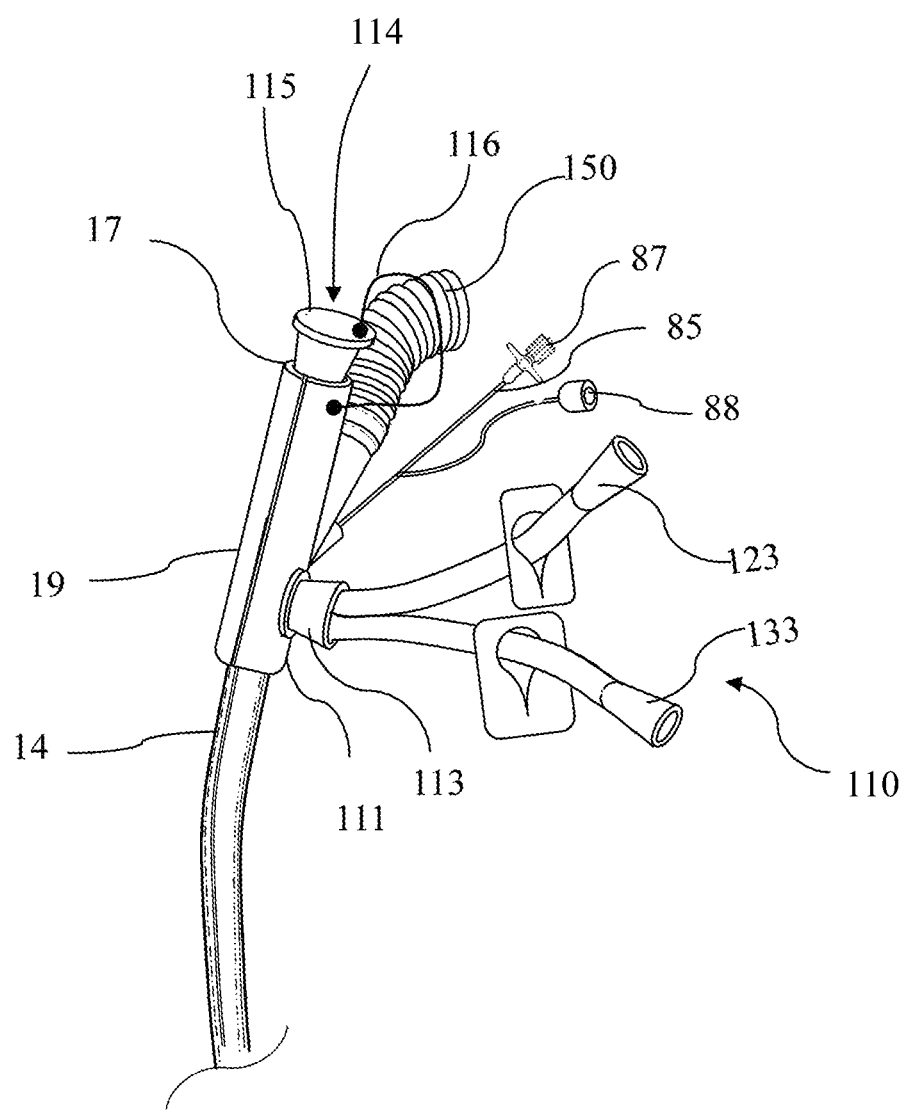

FIG. 17B is a perspective view of an alternate embodiment of the present invention depicting endoscope accessory with no endoscope in the overtube and the irrigation/drainage port is capped and the proximal end of the overtube is closed using a cap plug attached to a string.

Figure 17C:
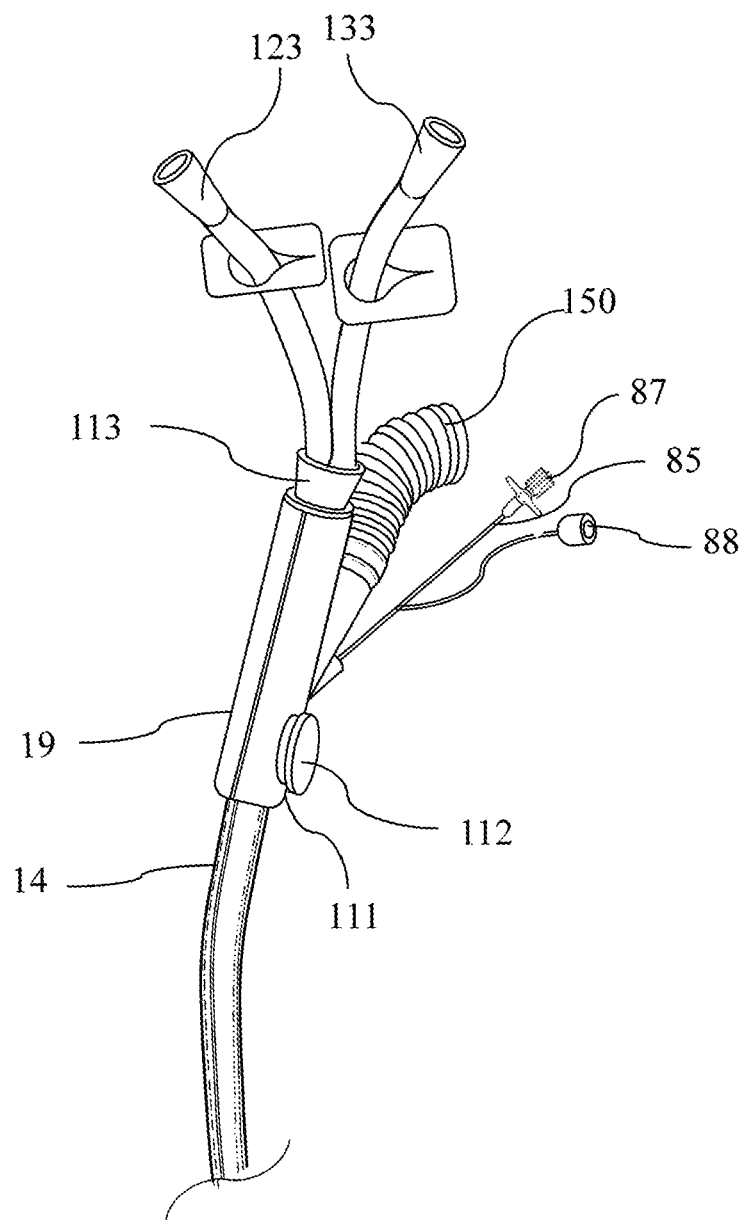

FIG. 17C is a perspective view of an alternate embodiment of the present invention depicting endoscope accessory with no endoscope in the overtube and the irrigation/drainage port is capped and the proximal end of the overtube is connected to an irrigation/drainage tube connector.

V. DETAILED DESCRIPTION OF THE INVENTION

Before explaining some aspects of embodiment of the present invention in detail, it is to be understood that the present invention is not limited in its application to the details of arrangements of the components set forth in the following description. As can be appreciated by those skilled in the arts, the present invention is capable of other embodiments and of being practiced and carried out in various ways. Also, it is to be understood that the phraseology and terminology employed herein are for the purpose of description and should not be regarded as limiting. It is also to be understood that where ranges are provided for various aspects of the invention and for examples, they are approximate ranges and are not to be limiting except where noted otherwise.

Unless defined otherwise, all technical and scientific terms used herein have the same meaning as commonly understood by one of ordinary skill in the art to which this invention belongs. Moreover, the singular forms "a", "an", and "the" include plural referents unless the context clearly dictates otherwise.

Use of the word endoscope includes any device that would benefit from the use of an endoscopy accessory made according to the principles of the invention for examination, diagnosis or treatment.

Use of the word endoscope or echoendoscope is meant to include both unless context dictates otherwise.

Use of the word gastrointestinal tract is a generic form of a body cavity that can be visualized by endoscopic exam. Those skilled in the art, know that the proposed device can be use in any other body cavity that can be examined by endoscopes including but not limited to all other visceral organs and non-visceral body organ.

Use of the word water is also meant to include any useful fluid, including but not limited to medications or gels.

Additionally, while the word examination is used, it is meant to include also diagnosis, treatment or therapy as may be the case.

Figure 1:
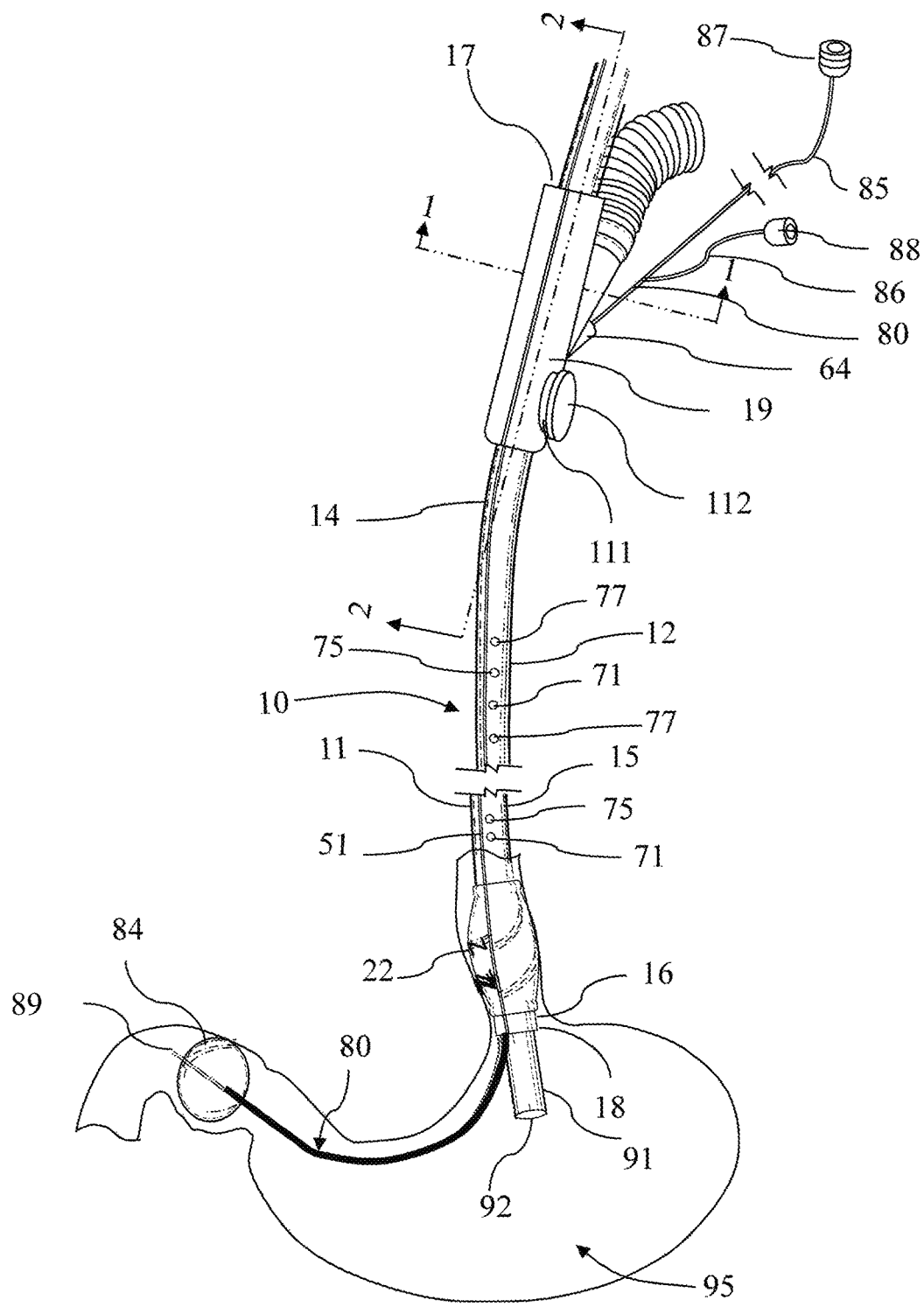
FIG. 1 is a schematic illustration of the device within the upper gastrointestinal tract.

According to certain embodiments of the present invention, an endoscope accessory 10 can include:

A—Overtube:

As it is depicted in FIG. 1, an overtube 11, as shown in FIG. 1, which can define an essentially cylindrical central through passageway for receiving there within an endoscope or echoendoscope shaft 91 and then is inserted inside a body cavity such as gastrointestinal tract.

Overtube 11 has an external surface 12 and an internal surface (not shown in FIG. 1), a proximal end portion 14, a midportion 15, a distal end portion 16, a proximal opening 17 and a distal opening 18. Overtube 11 can include at least one handle 19 at its proximal end portion 14. Handle 19 on the external surface 12 at the proximal end portion 14 of the overtube 11 is for grasping and manipulation of the overtube 11 within the body cavity. Handle 19 is also a hub where a plurality of external inflation tubes, quick connect fitting, occlusion balloon quick connect fitting (not shown in FIG. 1) and irrigation/drainage port can connect to overtube 11 and can be used for connection of the overtube to inflation device, suction device, irrigation tubes or passage of therapeutic tools through overtube 11.

The length of overtube 11 can be long enough so that when the distal end portion 16 of the overtube 11 is secured inside the body cavity, the overtube proximal end portion 14 stays out of the body cavity and allows grasping of the handle 19 and manipulation of overtube 11 for proper positioning of the overtube distal end portion 16 within the body cavity by the operator. The diameter of overtube 11 can be wide enough to freely receive a regular endoscope or echoendoscope shaft 91 therewithin. Within the body cavity, the endoscope tip 92 extends beyond overtube 11 distal end portion 16, as shown in FIG. 1, for detailed examination of the body cavity. Overtube 11 can include a longitudinal seam 51 along its entire length that allows opening of overtube 11 along its entire length for placing the endoscope shaft 91 within overtube 11 without the need for removing endoscope shaft 91 from the body cavity. The irrigation/drainage port 111 projects over the handle 19 and is capped by the irrigation/drainage port cap 112.

The overtube 11 can further include at least a suction conduit port 71 situated on the external surface 12 of the overtube 11 between the inflatable positioning ring 22 and the proximal end portion 14 of the overtube 11. The suction conduit port 71 can be used to drain air or water from the body cavity accumulated proximal to positioning ring 22.

The overtube 11 can further include at least one flushing port 75 situated on the external surface 12 of the overtube 11 between the inflatable positioning ring 22 and the proximal end portion 14 of the overtube 11. The flushing conduit (not shown) terminates distally at a flushing port 75 (shown in FIGS. 1 and 16) and proximally extends to quick connect fitting 140 on the handle 19 at proximal end portion 14 of overtube 11 and can be connected to automated control system 180. The flushing port 75 can be used to inject fluid or gas to flush the body cavity proximal to the inflatable positioning ring 22 in the body cavity.

The overtube 11 can further include at least a fenestration hole 77 situated on the external surface 12 of the overtube 11 between the inflatable positioning ring 22 and the proximal end portion 14 of the overtube 11. The fenestration hole 77 connects the external surface 12 of the overtube 11 to the internal surface 13 of the overtube 11, between the inflatable positioning ring 22 and the proximal end portion 14 of the overtube 11. The fenestration hole/s can allow a passive passage of fluid, secretion and gas from the lumen of gastrointestinal tract proximal to the inflatable positioning ring 22 to the lumen of the overtube for drainage of the body cavity.

Figure 2:
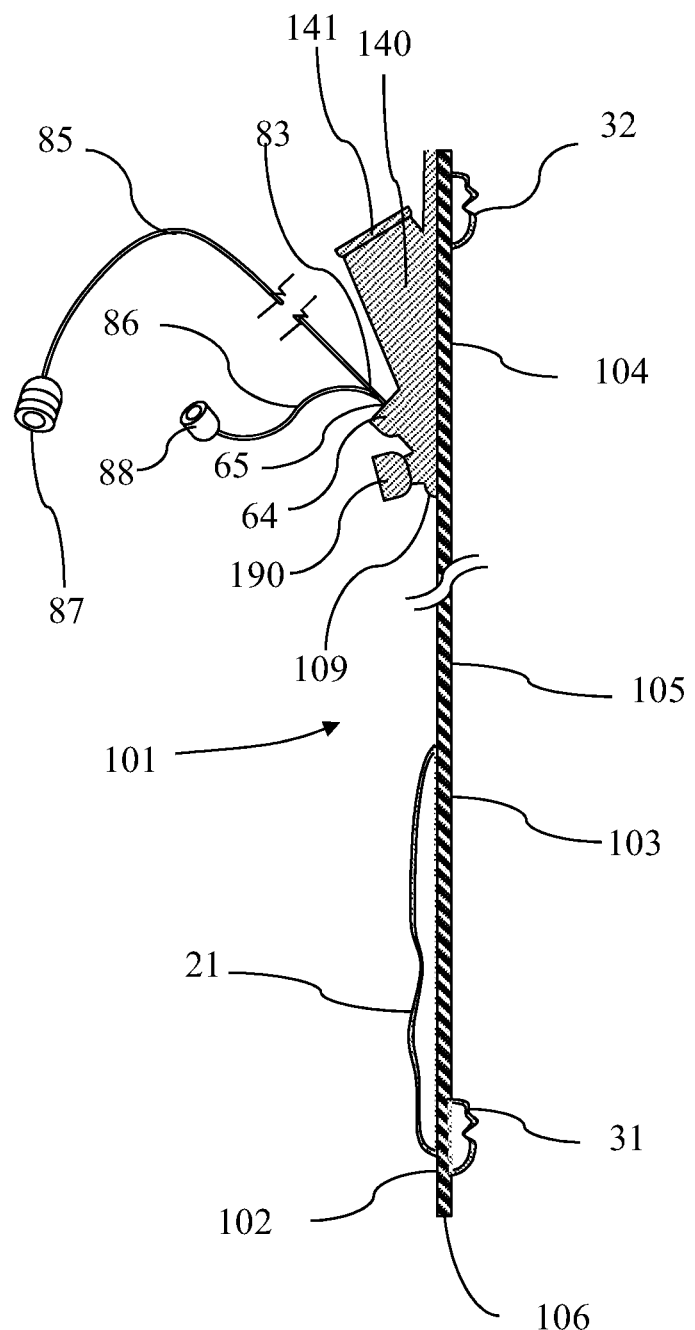
FIG. 2 is a longitudinal sectional view of the device shown in FIG. 1 taken along plane 2-2 when the seam is open.

As it is depicted in FIG. 2, overtube 11 of the endoscope accessory 10 is composed of a flexible elongated sheet 101, sized to removably envelop the flexible endo scope or echoendoscope shaft, having face 102 and face 103, a proximal end portion 104, a midportion 105, a distal end portion 106, and opposed longitudinal edge portions 107 and 108 (neither are shown in FIG. 2) that can coact reversibly to form a flexible overtube 11 (FIG. 1). Face 103 forms inner surface 13 (shown in FIG. 4) of overtube 11 which defines a central through passageway for receiving therewithin the endoscope or echoendoscope shaft 91 which can be inserted inside a body cavity such as the gastrointestinal tract (FIG. 1).

The sheet 101 is further provided with a strip 109 on face 102 of the sheet 101, which can extend across the entire width of the sheet 101 at the proximal end portion 104 of the sheet 101. An inflatable pocket 21 on face 102 of sheet 101, extends across the entire width of sheet 101 at the distal end portion 106 of the sheet 101, forming an inflatable positioning ring 22 (FIG. 1) on external surface 12 of overtube 11.

Figure 4:
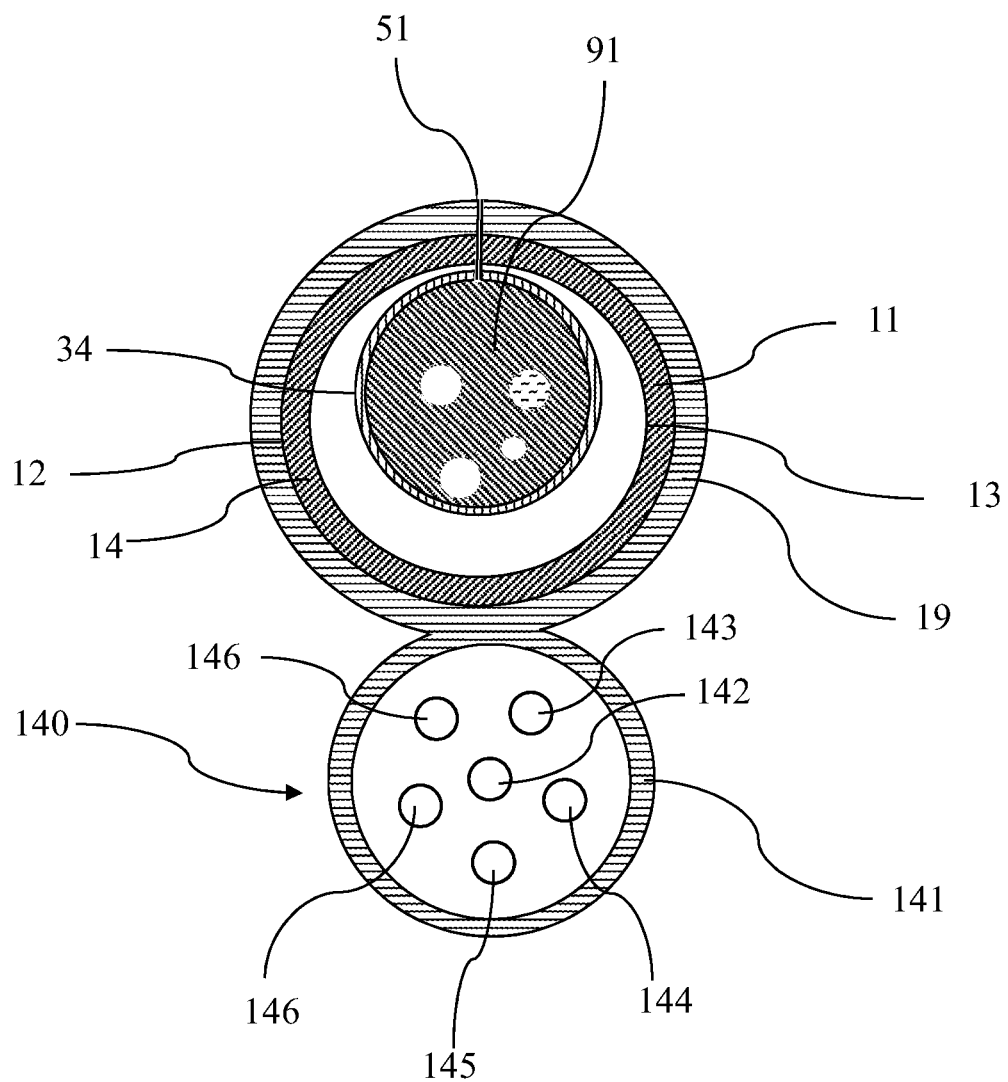
FIG. 4 is a sectional view of the device shown in FIG. 1 taken along plane 1-1 when the seam is closed.
Figure 5:
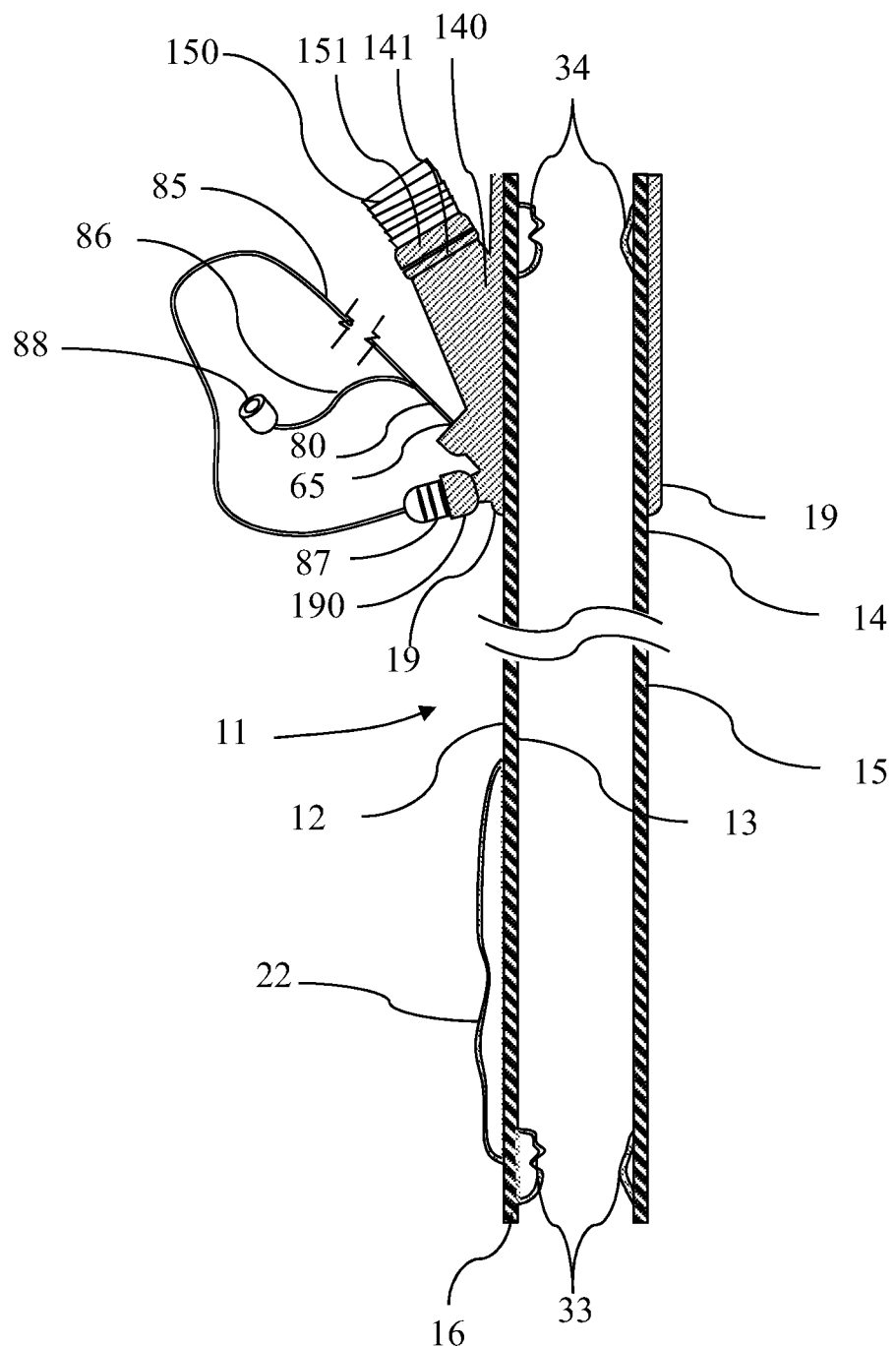
FIG. 5 is a longitudinal sectional view of the device shown in FIG. 1 taken along plane 2-2, when seam is closed and the umbilical extension tube and occlusion balloon quick connect fitting are connected to the overtube.

As it is depicted in FIG. 2, at least one inflatable band 31 can be located on face 103 of sheet 101 at distal end portion 106 of sheet 101. At least one inflatable band 33 can be located on face 103 of sheet 101 at proximal end portion 104 of sheet 101. More inflatable bands can be located on face 103 of sheet 101 at mid-portion 105 of sheet 101 (not shown). When opposed longitudinal edge portions 107 and 108 (neither are shown in FIG. 2) coact to form a flexible overtube 11, the inflatable band 31 forms inflatable sealing band 32 at the distal end portion 16, internal surface 13 of flexible overtube 11 (FIG. 5) and the inflatable band 33 forms inflatable sealing band 34 at the proximal end portion 14, on the internal surface 13 of flexible overtube 11 (FIGS. 4 and 5).

Inflatable sealing band 32 or 34 can be inflated independently using sealing band inflation tubes (not shown) that are carried by overtube 11 and terminate in quick connect fitting 140 at the handle 19 of the overtube 11.

An alternative embodiment in sheet 101 can be an elongated elastomeric bead (not shown) on face 103 of sheet 101 that can be provided in lieu of inflatable pocket 31, extending across entire width of the sheet at proximal end portion 104 of sheet 101. Elastomeric bead 36 can form an elastomeric sealing bead on internal surface 13 of overtube 11 (not shown) when opposed longitudinal edge portions 107 and 108 coact to form overtube 11. Those skilled in arts can quickly understand, elastomeric bead 36 can be multiple, replace one or more sealing bands and be located at any point along the length of overtube 11.

On face 102, there can be a strip 109 disposed at proximal end portion 104 of sheet 101. The strip 109 is supplied with a quick connect fitting 140, occlusion balloon quick connect fitting 190 and catheter port projection 64 that all projects over strip 109. When opposed longitudinal edge portions 107 and 108 (neither are shown in FIG. 2) coact to form a flexible overtube 11, the strip 109 forms handle 19 on the external surface 12 of flexible overtube 11 (FIGS. 1 and 4 and 5).

As it is depicted in FIG. 2, the strip 109 of the overtube 101 of the endoscope accessory 10 is supplied with a quick connect fitting 140. The quick connect fitting 140 allows a detachable coupling of multiple tubes at the proximal end portion 14 of the overtube 11 into an umbilical extension tube (not shown in FIG. 2). The umbilical extension tube has one quick connect fitting on each end and serves as an extension tubing to connect the overtube 11 to inflation, irrigation, insufflation or suction devices. The male-female interface (The ring connection 141 over the handle is only shown in this figure) of the quick connect fitting allows a detachable connection of multiple ports and tubes with one locking action.

As it is depicted in FIG. 2, a catheter passageway (not shown) can extend outward as a catheter port projection 64 over the strip 109 at the proximal end portion 104 of sheet 101. Catheter passageway terminates in a catheter entrance port 65 at the tip of catheter port projection 64. Catheter passageway defines a through passageway for receiving therewithin a catheter or other endoscopic accessories. After opposed longitudinal edge portions 107 and 108 coact to form flexible overtube 11, catheter passageway can be used for passing a catheter or an endoscope accessory device by overtube 11. A catheter or endoscopic accessory device can be inserted into catheter entrance port 65 on catheter port projection 64 and passed through catheter passageway and exit from the catheter exit port 61 (shown in FIG. 11A) inside the body cavity, such as the gastrointestinal tract.

Figure 3:
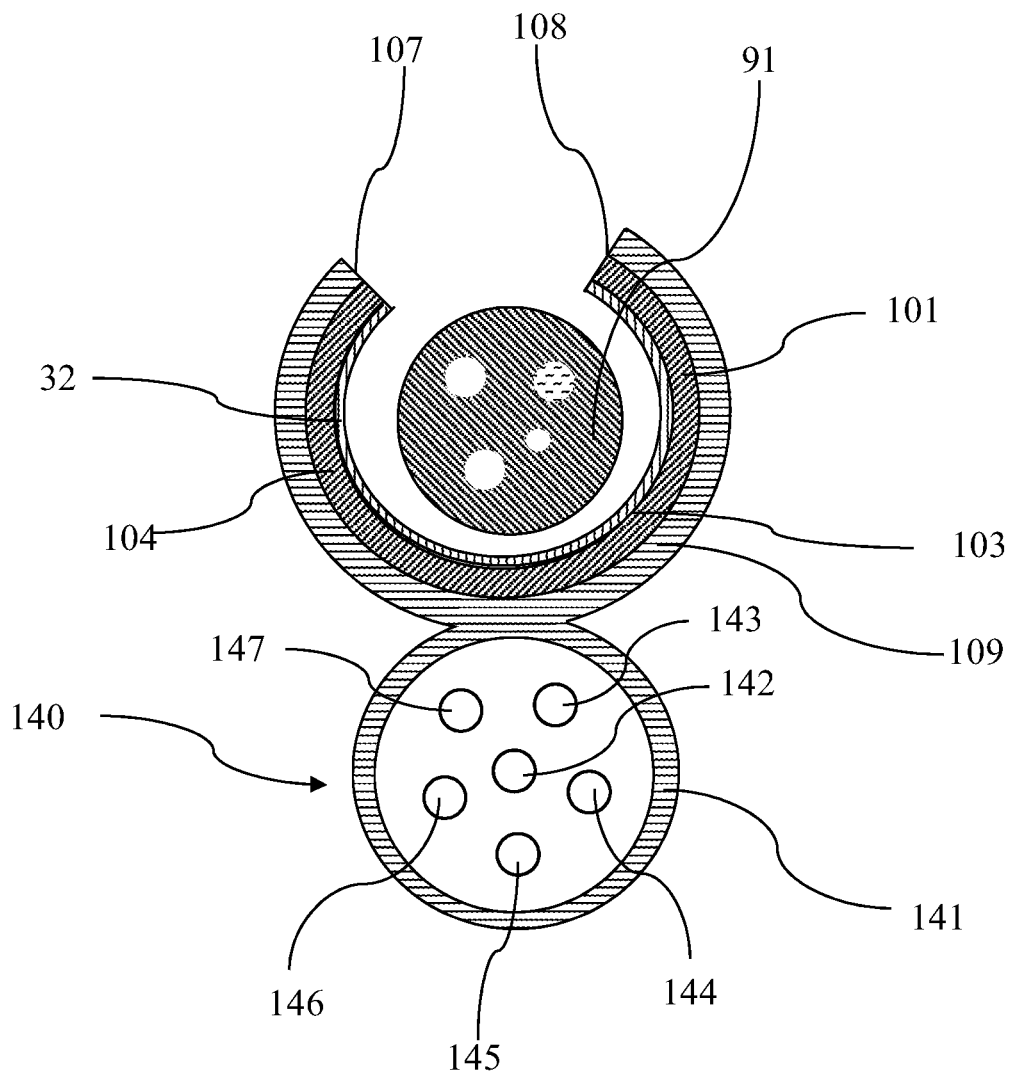
FIG. 3 is a sectional view of the device shown in FIG. 1 taken along plane 1-1 when the seam is open.

As it is depicted in FIG. 3, the strip 109 of the sheet 101 of the endoscope accessory 10 is supplied with a quick connect fitting 140. This figure also shows an inflatable band 33 attached to the internal surface 103, at the proximal end portion 104 of the sheet 101. The edges of the inflatable band 33 ends at the opposed longitudinal edge portions 107 or 108 of the sheet 101.

As it is depicted in FIG. 4, when opposed longitudinal edge portions 107 and 108 coact to form a seam 51, the flexible overtube 11 is formed. Then, the strip 109 forms handle 19 on the external surface 12 of flexible overtube 11. After closure of seam 51, the inflated band 33 can be eccentric relative to longitudinal axis of overtube 11 in a way that inflatable sealing band 34 and overtube internal surface 13 create internal tangent circles. The tangent point of these two circles can be at longitudinal seam 51. This allows a better sealing created by inflatable sealing band 34 over endoscope shaft 91. The ports and tubes 142-146 can be detachably attached through the quick connect fitting 140 used for purpose of inflation, insufflation, irrigation, suctioning.

As it is depicted in FIG. 5, the handle 19 of the overtube 11 of the endoscope accessory 10 is supplied with a quick connect fitting 140. The quick connect fitting 140 allows a detachable coupling of multiple tubes at the proximal end portion 14 of the overtube 11 into an umbilical extension tube 150. The umbilical extension tube 150 has one quick connect fitting on each end and serves as an extension tubing to connect the endoscope accessory 10 to and automated control system (not shown in FIG. 5). The ring connection 141 over the handle 19 of the quick connect fitting 140 allows a detachable connection to the umbilical extension tube 150 to a ring 151 in a male-female fashion.

In this figure, also it is shown, the occlusion balloon catheter. The occlusion balloon inflation tube 85 joins occlusion catheter suction tube 86 carried by occlusion balloon catheter 80. The occlusion balloon inflation tube 85 terminates at an occlusion balloon quick connect fitting 87. The occlusion catheter suction tube 86 terminates at an occlusion catheter suction connection piece 88. The occlusion balloon quick connect fitting 87 connects to the interface of the quick fitting 190 on the handle 19 of the overtube 11. The occlusion catheter suction tube 86 terminates at an occlusion catheter suction tip 89 (shown in FIGS. 1 and 16A-16E) that can be used to drain air or water accumulated within the body cavity distal to inflatable occlusion balloon 84 (shown in FIGS. 1 and 16A-16E).

Figure 6:
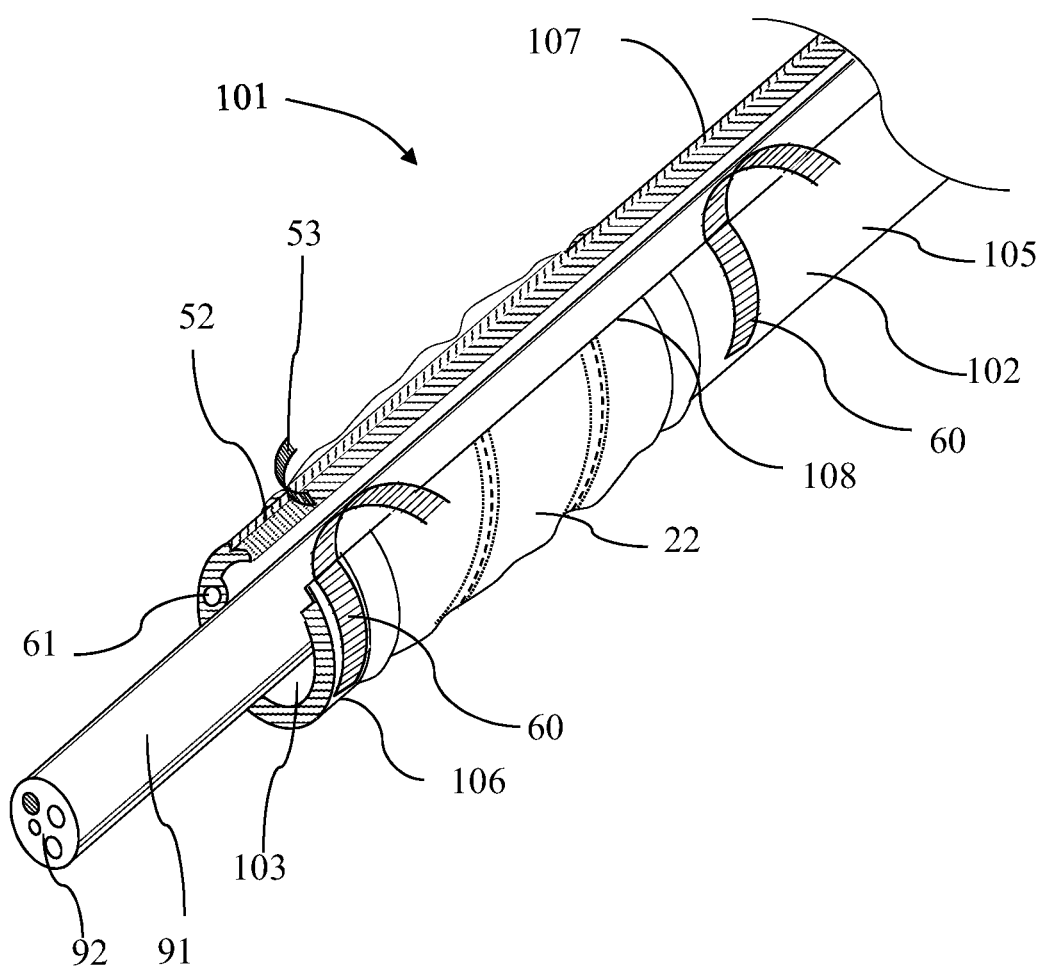
FIG. 6 is a partial schematic illustration of the endoscope accessory showing the process of closing the seam by removing the release sheet off of the adhesive tapes or self-fusing silicon tape and tape straps to attach the opposing longitudinal edge portions and create the seam.

As it is depicted in FIG. 6, sheet 101 can wrap around or envelop endoscope shaft 91 while opposed longitudinal edge portions 107 and 108 are still apart. The opposed longitudinal edge portions 107 and 108 can be supplied with an adhesive 52 covered by a release sheet 53. After removal of release sheet 53 from adhesive 52 at least one of the opposed longitudinal edge portions 107 and 108, opposed longitudinal edge portions 107 and 108 can be overlapped to form longitudinal seam 51 along the entire length of overtube 11 (shown in FIG. 1) to form an essentially cylindrical and hollow member. The opposed longitudinal edge portions 107 and 108 can be further be supported with adhesive straps 60 that is permanently adhered on the outer surface 102 or inner surface 103 of the sheet 101 on one side of the tube edge and crosses over the seam 51 and adheres to the outer surface 12 of the overtube 11 to further strengthen the seam 51.

Figure 7A:
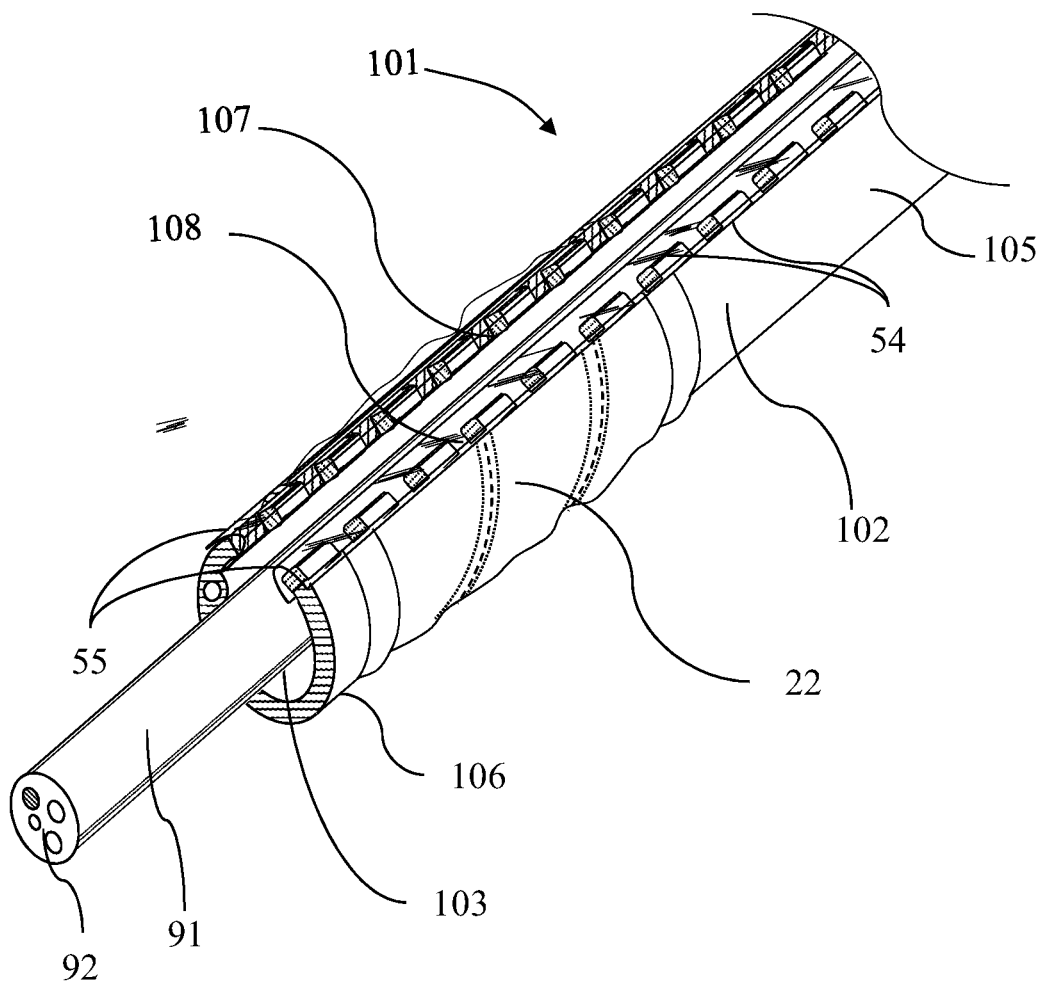
FIG. 7A is a partial schematic illustration of the endoscope accessory showing spaced magnets and magnet covers at the longitudinal edge portions.
Figure 7B:
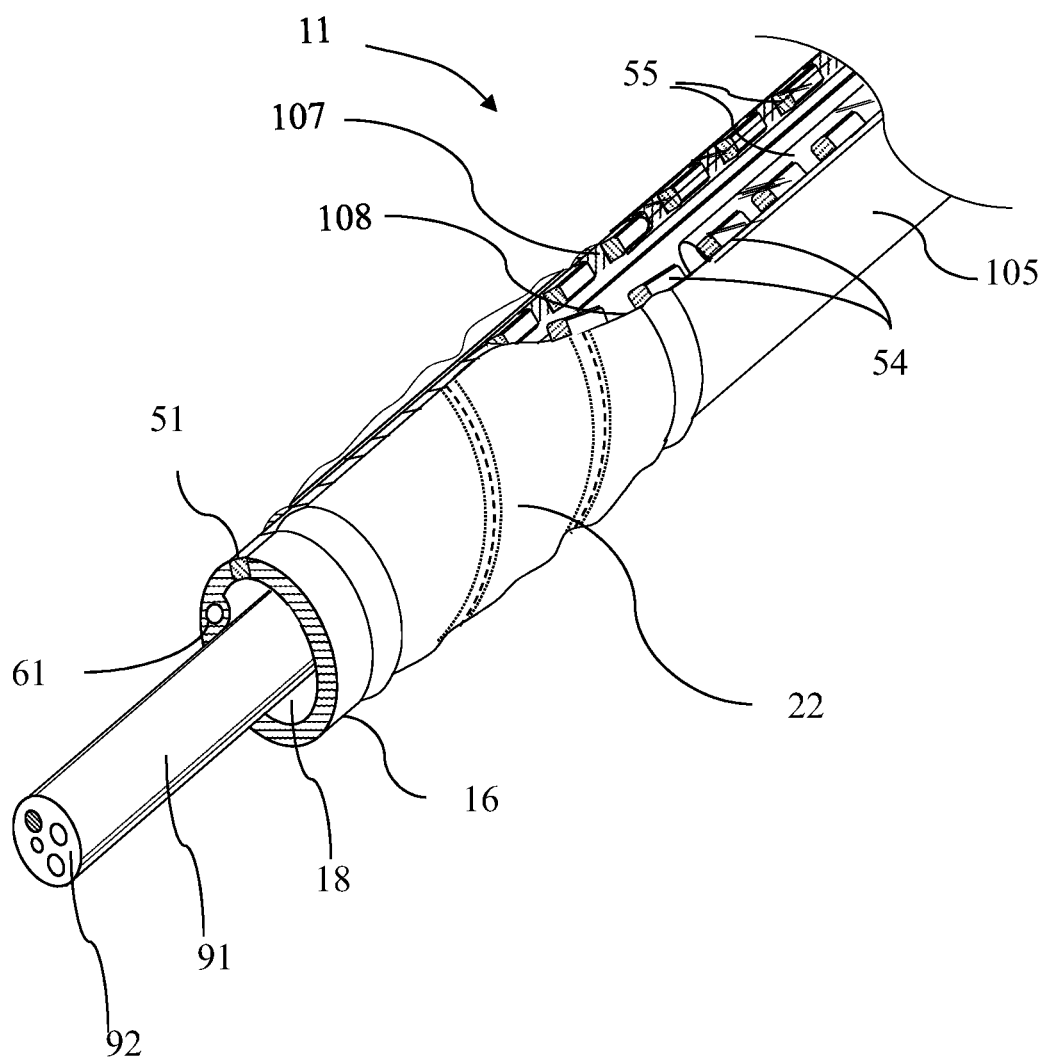
FIG. 7B is a partial schematic illustration of the endoscope accessory showing spaced magnets and magnet covers at the longitudinal edge portions after placement of the endoscope shaft and partial closure of the longitudinal seam.

An alternative embodiment of sheet 101 is depicted in FIGS. 7A and 7B. As it is shown in FIG. 7A, the closure can include a plurality of spaced magnets 54 that are provided in lieu of adhesive 52 and release sheet 53, carried by each longitudinal edge portions 107 and 108 along entire length of sheet 101 for coacting with the opposed edge portion. Spaced magnets 54 on longitudinal edge portions 107 are interspersed with spaced magnets on longitudinal edge portion 108 (FIG. 8B). The inflatable pocket 21 and the inflatable band 31 are offset from magnets 54. To avoid activation of the magnets 54 before placing endoscope shaft 91 within sheet 101, longitudinal edge portions 107 and 108 can be supplied with at least one longitudinal slit sleeve magnet cover 55. Magnets 54 can coact with the opposed longitudinal edge portion magnets 54 when magnet covers 55 are removed by longitudinal retraction of the magnet cover 55 from longitudinal edge portions 107 and 108.

As it is depicted in FIG. 7B, when magnet covers 55 are removed partially by longitudinal retraction of the magnet cover 55 proximally, distal end portion 106 of sheet 101 magnets 54 at the opposed longitudinal edge portions 107 and 108 coact. The coacting magnets 54 are in the form of spaced magnet pieces that are positioned next to each other in a row. The magnet pieces 54 are spaced apart to create a zipper closure that assembles longitudinal seam 51 starting from distal end portion 16 of overtube 11. Repeating this sequence closes longitudinal seam 51 along entire length of flexible overtube 11 and overtube 11 forms around endoscope shaft 91.

Figure 8A:
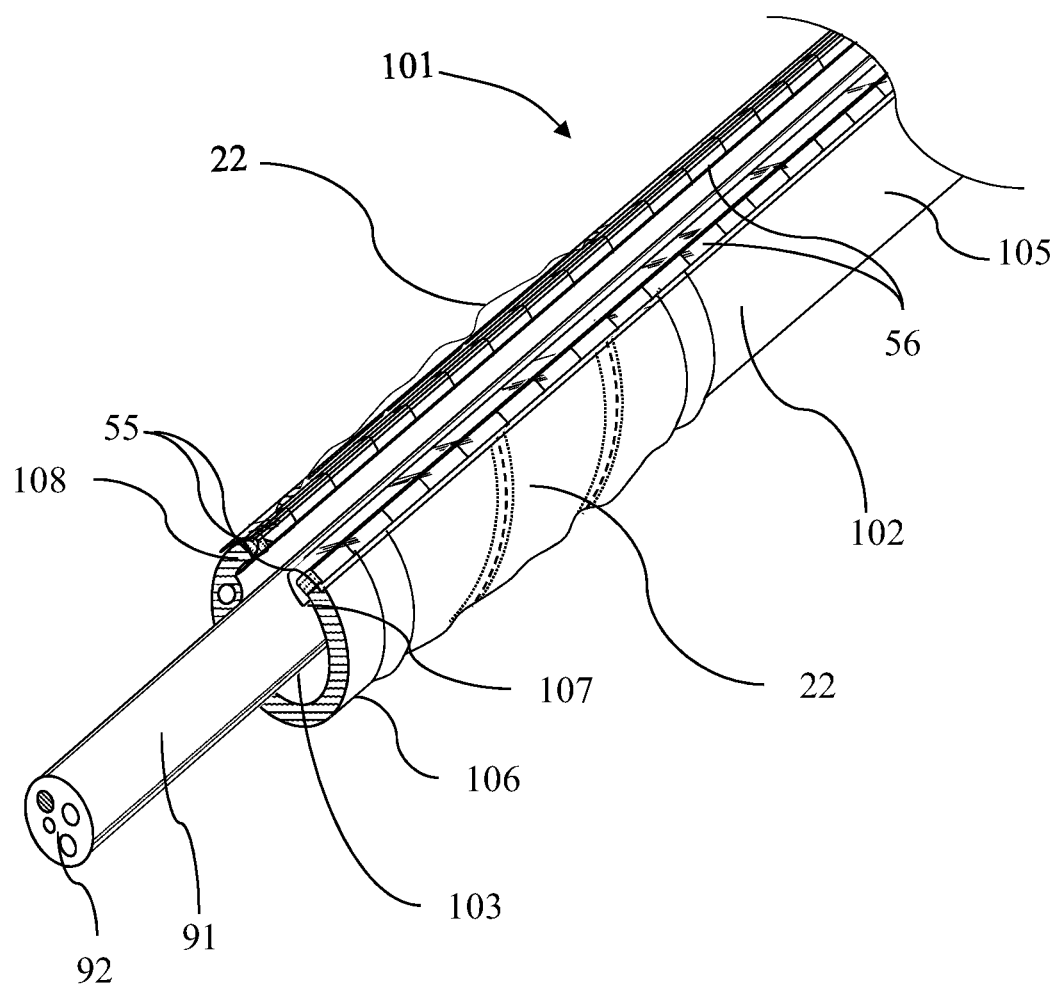
FIG. 8A is a partial schematic illustration of the endoscope accessory showing magnet strings at the longitudinal edge of the tube and magnet covers at the longitudinal edge portions.
Figure 8B:
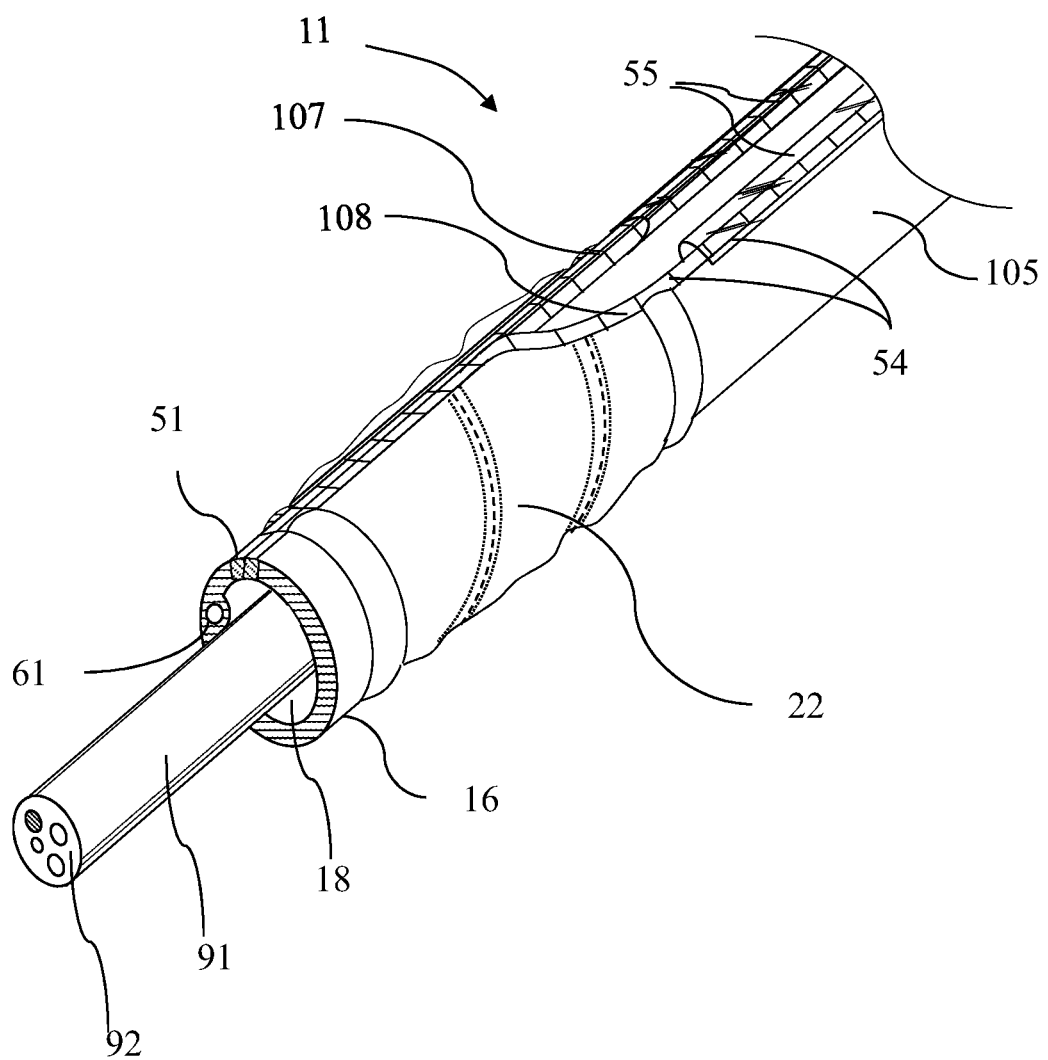
FIG. 8B is a partial schematic illustration of the endoscope accessory showing magnet strings at the longitudinal edge and magnet covers at the longitudinal edge portions after placement of the endoscope shaft and partial closure of the longitudinal seam.

An alternative embodiment of sheet 101 is depicted in FIGS. 8A and 8B. As it is shown in FIG. 8A, the closure can include a plurality of non-spaced magnets 56 that are provided in lieu of adhesive 52 and release sheet 53 or spaced magnets 54, carried by each longitudinal edge portions 107 and 108 along entire length of sheet 101 for coacting with the opposed edge portion. The plurality of non-spaced magnets 56 on longitudinal edge portions 107 and 108 are attached individually at the edge portion 107 and 108. The inflatable pocket 21 and the inflatable band 31 are offset from non-spaced magnets 56. To avoid activation of the non-spaced magnets 56 before placing endoscope shaft 91 within sheet 101, longitudinal edge portions 107 and 108 can be supplied with at least one longitudinal slit sleeve magnet cover 55. Non-spaced magnets 56 can coact with the opposed longitudinal edge portion non-spaced magnets 56 when magnet covers 55 are removed by longitudinal retraction of the magnet cover 55 from longitudinal edge portions 107 and 108.

As it is depicted in FIG. 8B, when magnet covers 55 are removed partially by longitudinal retraction of the magnet cover 55 proximally, distal end portion 106 of sheet 101 non-spaced magnets 56 at the opposed longitudinal edge portions 107 and 108 coact. The coacting non-spaced magnets 56 assembles longitudinal seam 51 starting from distal end portion 16 of overtube 11. Repeating this sequence closes longitudinal seam 51 along entire length of flexible overtube 11 and overtube 11 forms around endoscope shaft 91.

Figure 9A:
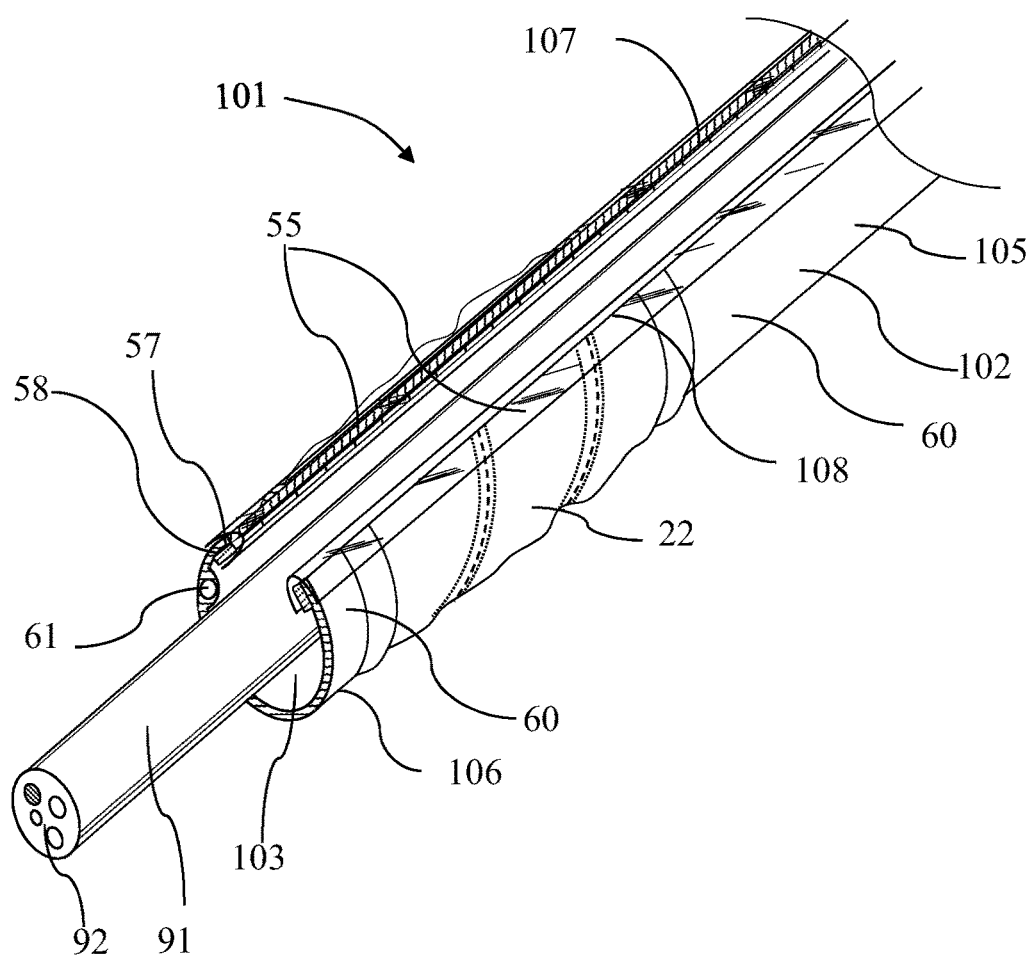
FIG. 9A is a partial schematic illustration of the endoscope accessory showing magnet strings under the longitudinal edge of the tube and magnet covers at the longitudinal edge portions.

An alternative embodiment of sheet 101 is depicted in FIGS. 9A, 9B, 9C and 9D. As it is shown in FIG. 9A, the closure can include a plurality of magnets in a form of a magnet strings 57 that are provided in lieu of adhesive 52 and release sheet 53 or spaced magnets 54, or non-spaced magnets 56 carried by each longitudinal edge portions 107 and 108 along entire length of sheet 101 for coacting with the opposed edge portion. The magnet strings 57 is composed of a plurality of magnet bids that are held together in a thin tube like structure 58. Each tube like structures 58 containing magnet strings 57 is attached at the edge, under the edge or above the edge at the longitudinal edge portions 107 and 108. The inflatable pocket 21 and the inflatable band 31 are offset from magnet strings 57. To avoid activation of the magnet string 57 before placing endoscope shaft 91 within sheet 101, longitudinal edge portions 107 and 108 can be supplied with at least one longitudinal slit sleeve magnet cover 55. Magnet string 57 can coact with the opposed longitudinal edge portion magnet string 57 when magnet covers 55 are removed by longitudinal retraction of the magnet cover 55 from longitudinal edge portions 107 and 108.

Figure 9B:
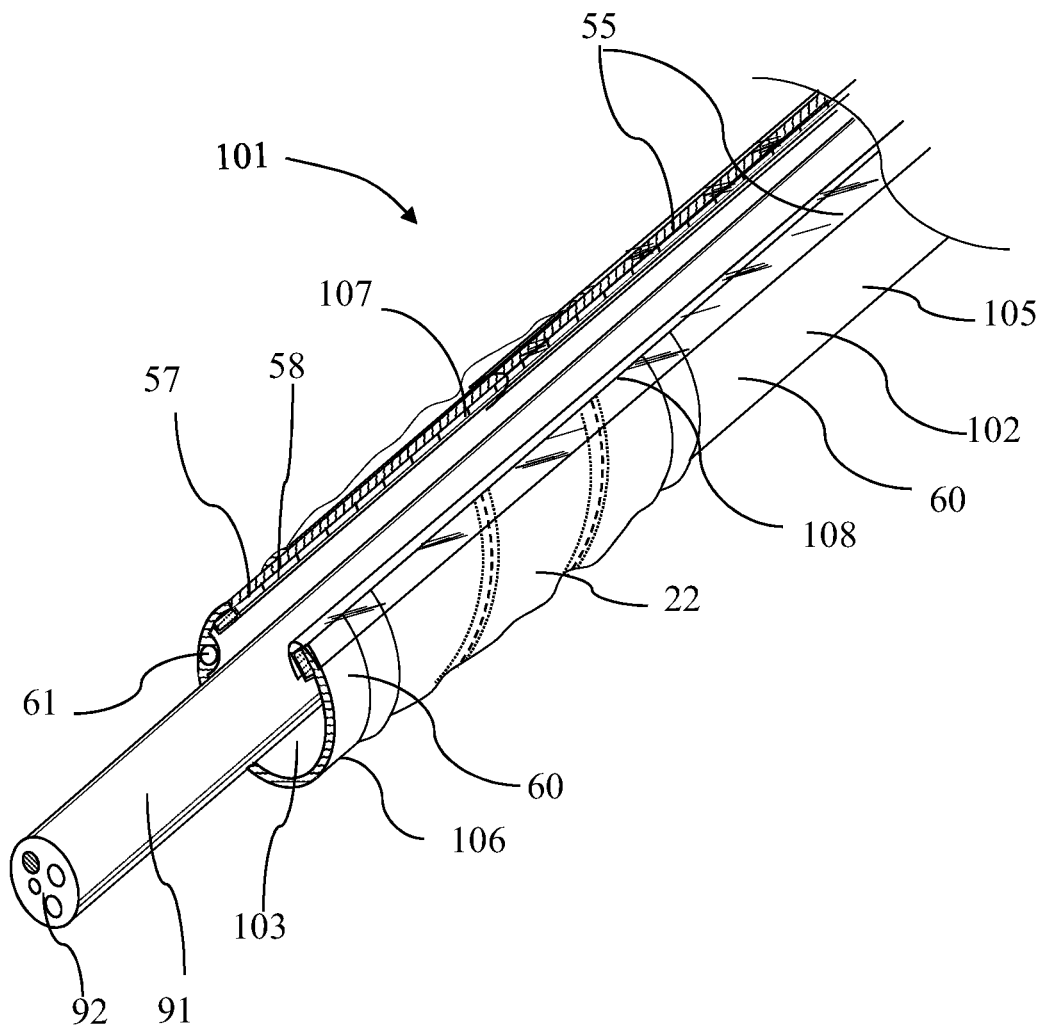
FIG. 9B is a partial schematic illustration of the endoscope accessory showing magnet strings under the longitudinal edge of the tube and one magnet cover is being removed by pulling back from one side at the longitudinal edge portions.
Figure 9C:
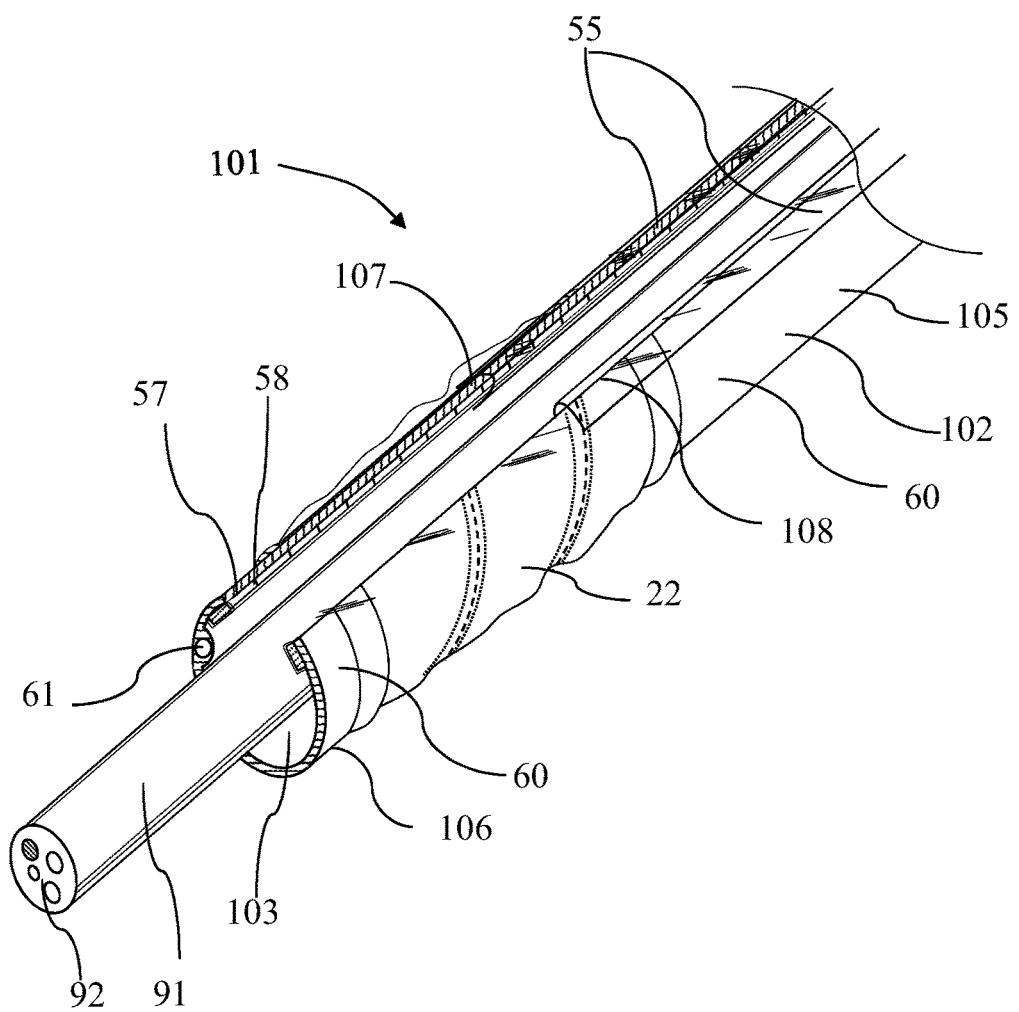
FIG. 9C is a partial schematic illustration of the endoscope accessory showing magnet strings under the longitudinal edge of the tube and both magnet covers are being removed by pulling back from both sides at the longitudinal edge portions.

As it is depicted in FIG. 9B, when magnet covers 55 are removed partially by longitudinal retraction of the magnet cover 55 proximally, distal end portion 106 of sheet 101 magnet string 57 at the opposed longitudinal edge portions 107 followed by the same on the opposed longitudinal edge portions 108 (FIG. 9C), the magnet strings 57 from both side coact. The coacting magnet string 57 assembles longitudinal seam 51 starting from distal end portion 16 of overtube 11

Figure 9D:
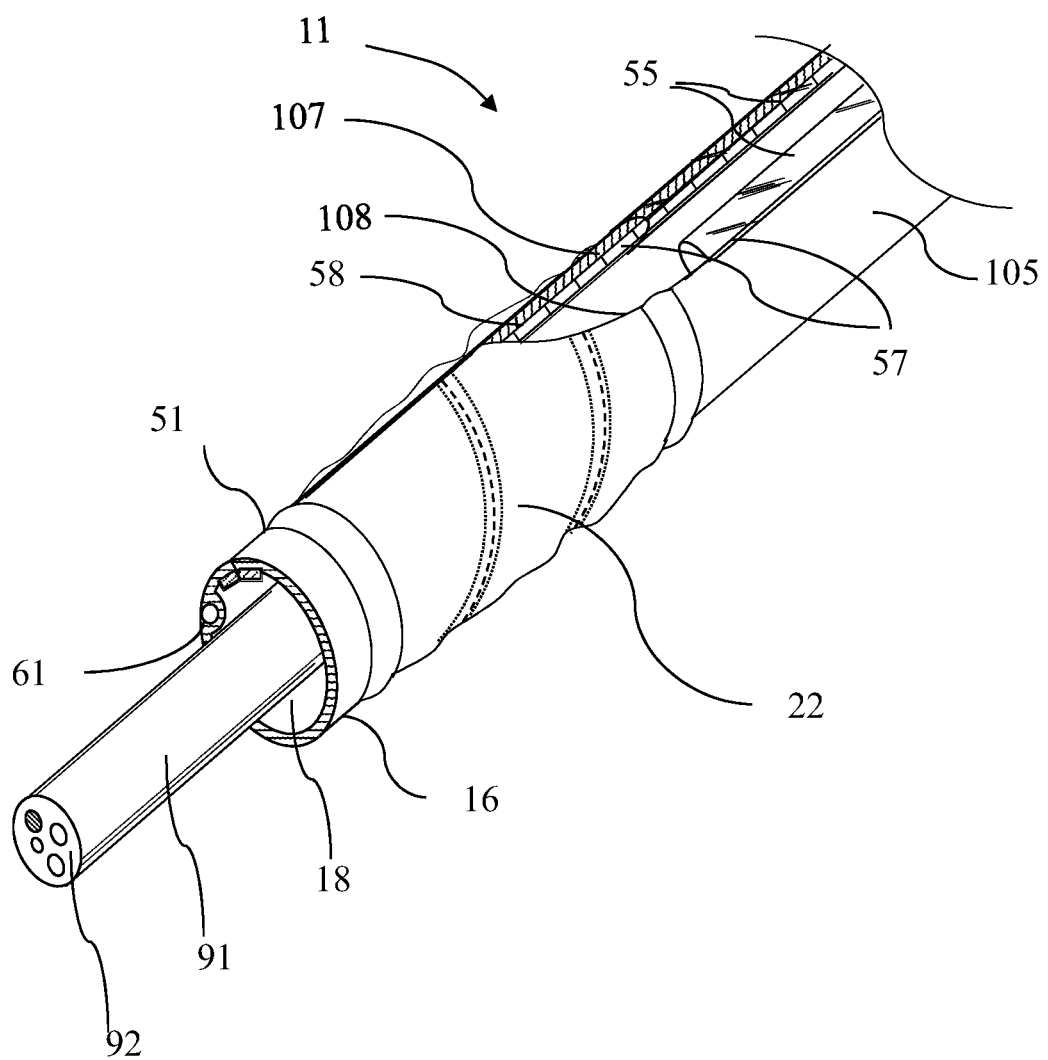
FIG. 9D is a partial schematic illustration of the endoscope accessory showing magnet strings under the longitudinal edge and magnet covers at the longitudinal edge portions after placement of the endoscope shaft and partial closure of the longitudinal seam.

(FIG. 9D). Repeating this sequence closes longitudinal seam 51 along entire length of flexible overtube 11 and overtube 11 forms around endoscope shaft 91.

An alternative embodiment of sheet 101 is depicted in FIGS. 10A and 10B. As it is shown in FIG. 10A, the closure can include a plurality of magnets in a form of spaced magnets 54, magnets 55 or magnet strings 57 that are provided in lieu of adhesive 52 and release sheet 53. The opposed longitudinal edge portions 107 and 108 can be further be supported with adhesive straps 60 that is permanently adhered on the outer surface 102 or inner surface 103 of the sheet 101 on one side of the tube edge and crosses over the seam 51 and adheres to the outer surface 12 of the overtube 11 to further strengthen the seam 51. To avoid activation of the spaced magnets 54, magnets 55 or magnet strings 57 before placing endoscope shaft 91 within sheet 101, longitudinal edge portions 107 and 108 can be supplied with at least one longitudinal slit sleeve magnet cover 55 (in this figure only one on the edge 108). Magnet 54, magnets 55 or magnet strings 57 can coact with the opposed longitudinal edge portion magnet string 57 when magnet cover 55 is removed by longitudinal retraction of the magnet cover 55 from longitudinal edge portion 108.

As it is depicted in FIG. 10B, when magnet cover 55 is removed partially by longitudinal retraction of the magnet cover 55 proximally, distal end portion 106 of sheet 101 magnet 54, magnets 55 or magnet strings 57 at the opposed longitudinal edge portions 107 and 108 coact. The coacting magnets assembles longitudinal seam 51 starting from distal end portion 16 of overtube 11. Repeating this sequence closes longitudinal seam 51 along entire length of flexible overtube 11 and overtube 11 forms around endoscope shaft 91. The opposed longitudinal edge portions 107 and 108 can be further be supported with adhesive straps 60 that is permanently adhered on the outer surface 102 or inner surface 103 of the sheet 101 on one side of the tube edge and crosses over the seam 51 and adheres to the outer surface 12 of the overtube 11 to further strengthen the seam 51.

An alternative embodiment of sheet 101 is depicted in FIGS. 11A and 11B. As it is shown in FIG. 11A, the closure can include a plurality of magnets in a form of a magnet string flap 59 that are provided in lieu of adhesive 52 and release sheet 53 or spaced magnets 54, non-spaced magnets 56, or magnet strings 57 carried by at least one longitudinal edge portions 107 and 108 along entire length of sheet 101 for coacting with the opposed edge portion. The magnet string flap 59 is composed of plurality of magnet bids that are hold together as a magnet string in a thin tube like structure 58 that is attached to the edge portion of the tube only along one longitudinal line and can swing on the longitudinal axis while attached to the edge portion 107 and 108. The magnet string flap is kept under the edge or above the edge at the longitudinal edge portions 107 and 108 using the magnet cover 55. The inflatable pocket 21 and the inflatable band 31 are offset from magnet string flap 59. In this particular configuration, the other edge portion 108 of the sheet 101 is supplied with a magnet string 57. To compensate for the height difference at least one edge 107 or 108 can have thicker end portion (in this figure edge 107). To avoid activation of the magnet string flap 59 or magnet string 57 before placing endoscope shaft 91 within sheet 101, longitudinal edge portions 107 and 108 can be supplied with at least one longitudinal slit sleeve magnet cover 55. Magnet string flap 59 can coact with the opposed longitudinal edge portion magnet string 57 when magnet covers 55 are removed by longitudinal retraction of the magnet cover 55 from longitudinal edge portions 107 and 108.

As it is depicted in FIG. 11B, when magnet covers 55 are removed partially by longitudinal retraction of the magnet cover 55 proximally, distal end portion 106 of sheet 101 magnet string flap 59 is released. This allows the distal end portion of the magnet string flap 59 on the edge portion 107 swings toward the opposed edge portion 108 magnet string 57. The coacting magnet string 57 assembles longitudinal seam 51 starting from distal end portion 16 of overtube 11. Repeating this sequence closes longitudinal seam 51 along entire length of flexible overtube 11 and overtube 11 forms around endoscope shaft 91.

An alternative embodiment of sheet 101 is depicted in FIGS. 12A, 12B, 12C and 12D. As it is shown in FIG. 12A, the closure can include a plurality of magnets in a form of a magnet string flaps 59 that are provided in lieu of adhesive 52 and release sheet 53 or spaced magnets 54, non-spaced magnets 56, or magnet strings 57 carried by longitudinal edge portions 107 and 108 along entire length of sheet 101 for coacting with the opposed edge portion. The magnet string flap 59 is composed of plurality of magnet bids that are hold together as a magnet string in a thin tube like structure 58 that is attached to the edge portion of the tube only along one longitudinal line and can swing on the longitudinal axis while attached to the edge portion 107 and 108. The magnet string flap is kept under the edge or above the edge at the longitudinal edge portions 107 and 108 using the magnet cover 55. The inflatable pocket 21 and the inflatable band 31 are offset from magnet string flap 59. To avoid activation of the magnet string flap 59 before placing endoscope shaft 91 within sheet 101, longitudinal edge portions 107 and 108 can be supplied with longitudinal slit sleeve magnet cover 55. Magnet string flap 59 can coact with the opposed longitudinal edge portion magnet string flap 59 when magnet covers 55 are removed by longitudinal retraction of the magnet cover 55 from longitudinal edge portions 107 and 108.

As it is depicted in FIG. 12B, when magnet covers 55 are removed partially by longitudinal retraction of the magnet cover 55 proximally, distal end portion 106 of sheet 101 magnet string flap 59 is released. This allows the distal end portion of the magnet string flap 59 on the edge portion swings toward the opposed edge portion followed by the same on the opposed longitudinal edge portions (FIG. 12C). The coacting magnet string flaps 59 assembles longitudinal seam 51 starting from distal end portion 16 of overtube 11 (FIG. 12D). Repeating this sequence closes longitudinal seam 51 along entire length of flexible overtube 11 and overtube 11 forms around endoscope shaft 91.

An alternative embodiment of sheet 101 is depicted in FIGS. 13A and 13B. As it is shown in FIGS. 13A and 13B, the closure can include a zipper 190 that is provided in lieu of adhesive 52 and release sheet 53 or spaced magnets 54, non-spaced magnets 56, magnet strings 57 or magnet string flap 59 carried by longitudinal edge portions 107 and 108 along entire length of sheet 101 for approximation of the opposed edge portions. The zipper 190 is an open ended zipper that is composed of two zipper tapes 191 and 192 (neither are shown) that are attached under or over the edge portion 107 and 108 of the tube, respectively. The zipper tape 191 has an insert pin 193 at its distal end and the zipper tape 192 has a box pin 194 that is permanently placed in a retaining box 195. The insert pin 193 can be removably placed in the retaining box 195 and then allow the slider 196 to be moved and engage the zipper teeth 197 on each side and close the zipper. The inflatable pocket 21 and the inflatable band 31 are offset from zipper 190.

As it is depicted in FIG. 13B, the engagement of the zipper tape 191 with zipper tape 192 from its distal end toward its proximal end, assembles longitudinal seam 51 starting from distal end portion 16 of overtube 11. Continuing to pull the slider 196 proximally closes longitudinal seam 51 along the entire length of flexible overtube 11 and overtube 11 forms around endoscope shaft 91.

An alternative embodiment of sheet 101 is depicted in FIGS. 14A and 14B. As it is shown in FIGS. 14A and 14B, the closure can include a toothless zipper 200 that is provided in lieu of adhesive 52 and release sheet 53 or spaced magnets 54, non-spaced magnets 56, magnet strings 57, magnet string flap 59 or zipper 190, carried by longitudinal edge portions 107 and 108 along entire length of sheet 101 for approximation of the opposed edge portions. The zipper 200 is an open ended toothless zipper that is composed of two zipper tapes 201 and 202 that are attached under or over the edge portion 107 and 108 of the tube, respectively. The zipper tape 200 has an insert pin 203 at its distal end and the zipper tape 202 has a box pin 204 that is permanently placed in a retaining box 205. The insert pin 203 can be removably placed in the retaining box 205 and the allow the slider 206 to be moved and engage the zipper locking edges 207 and 208 on each side and close the zipper. The inflatable pocket 21 and the inflatable band 31 are offset from zipper 190.

As it is depicted in FIG. 14B, the engagement of the zipper tape 201 with zipper tape 202 from its distal end toward its proximal end, assembles longitudinal seam 51 starting from distal end portion 16 of overtube 11. Continuing to pull the slider 206 proximally closes longitudinal seam 51 along entire length of flexible overtube 11 and overtube 11 forms around endoscope shaft 91.

A further alternative embodiment of sheet 101 could be other closure mechanism for the opposing longitudinal edge portion 107 and 108. This includes cooperating coupling structures (not shown) that can provide an interlocking closure mechanism in a tongue and groove, complementary beveled or stepped edges, silicon longitudinal flap, or a combination of mechanism such as magnets beads, magnet strings, adhesive tape, adhesive tape straps, self-fusing silicon tape or self-fusing silicon tape straps (neither is shown).

B—Catheter and Occlusion Balloon:

As it is depicted in FIG. 1, the occlusion balloon catheter 80 is connected to an occlusion balloon 84 at distal end portion. Occlusion balloon 84 can be mounted on occlusion balloon catheter 80 in preferably an asymmetrical manner but can also be mounted in an essentially symmetrical manner. In the asymmetrical form (not shown), the occlusion balloon catheter 80 is situated eccentric in relation to the occlusion balloon 84. Occlusion balloon 84 can be inflated by an occlusion balloon inflation tube 85 that can be carried by occlusion balloon catheter 80. An occlusion catheter suction tube 86 can also be carried by occlusion balloon catheter 80. At midportion of occlusion balloon catheter 80, occlusion balloon inflation tube 85 and occlusion catheter suction tube 86 can be disposed side-by-side. At proximal end portion of the occlusion balloon catheter 80, occlusion balloon inflation tube 85 and occlusion catheter suction tube 86 can be separated and terminate at an quick connect fitting 87 and the occlusion catheter suction connection piece 88, respectively. At distal end portion of occlusion balloon catheter 80, occlusion balloon inflation tube 85 communicates with occlusion balloon 84 and occlusion catheter suction tube 86 passes through occlusion balloon 84 to terminate at an occlusion catheter suction tip 89 that can be used to drain air or water accumulated within the body cavity distal to inflatable occlusion balloon 84.

Distal end portion of occlusion balloon catheter 80 can be independently positioned distal to distal end portion 16 of overtube 11 within the body cavity. Proximal end portion of occlusion balloon catheter 81 can extend out of catheter passageway entrance port 65 on a catheter passageway port projection 64 of overtube 11.

C—Automated Control System and Umbilical Extension Tube:

As it is dep15, the endoscope accessory 10 is supplied with an umbilical extension tube 150 and an automated control system 180.

The endoscope accessory 10 can further include at least one quick connect fitting (shown in previous figures). The quick connect fitting allows a detachable coupling of multiple tubes at the proximal end portion of the overtube into an umbilical extension tube 150. The umbilical extension tube 150 has one quick connect fitting 151 and 161 on each end and serves as an extension tubing to connect the overtube 11 to and automated control system 180 for inflation, irrigation, insufflation or suctioning. The male-female interface 141 to 151 and 161 to 171 of the quick connect fitting on each end of the umbilical extension tube 150 allows a detachable connection of multiple ports and tubes with one locking action. Examples of the ports and tubes that can be detachably attached through the quick connect fitting can include but not limited to inflation tube for positioning ring, inflation tube for sealing band/s, inflation tube for occlusion balloon, insufflation port for insufflation with gas, irrigation tube for flushing port, suction conduits and fluid/insufflation conduit.

The automated control system 180 has a power switch 181, multiple knobs 183, 185, 187, buttons 182, 184 and 186 and digital display 188 for monitoring, adjusting and controlling the various function of the overtube during the procedure based on the application.

D—Irrigation Tubes:

As it is depicted in FIG. 17A, handle 19 can define irrigation/drainage port 111 that is capped with a removable irrigation/drainage port cap 112 (FIG. 1). Irrigation/drainage port cap 112 can be removed when desired, and an irrigation tube system 110 can be connected through irrigation tube connector 113 to irrigation/drainage port 111 while the scope is within the over tube (FIG. 17A) or when the endoscope shaft 91 is removed from the overtube and an end cap 115 close the proximal end 17 of the overtube (FIG. 17B). A clean water irrigation tube 121 and a wastewater irrigation tube 131 can both terminates at the irrigation tube connector 113 side by side.

Clean water can be infused within the examination compartment 95 through the lumen of overtube 11 using clean water irrigation tube 121. The flow of water within clean water irrigation tube 121 can be controlled using a slit valve 122. Clean water irrigation tube 121 can be connected to a container (not shown) of fresh water during irrigation of examination compartment 95 using a connection piece 123.

Wastewater can be drained from the examination compartment 95 through the lumen of overtube 11 using wastewater irrigation tube 131. The flow of water within wastewater irrigation tube 131 can be controlled using a slit valve 132. Wastewater irrigation tube 131 can be connected to a container (not shown) of wastewater during the irrigation of examination compartment 95 using a connection piece 133.

Alternatively, as depicted in FIG. 17C, irrigation system 110 can be connected through irrigation tube connector 113 to proximal opening 17 of overtube 11 when endoscope shaft 91 is not in overtube 11. In this configuration, irrigation/drainage port 111 can be capped by irrigation/drainage port cap 112.

E—Operation.

Endoscope tip 92 can be inserted into a body cavity such as the gastrointestinal tract to reach to the desired location within the body cavity. At this time, endoscope accessory sheet 101 is wrapped around endoscope shaft 91 and opposed longitudinal edge portions 107 and 108 coact to form flexible overtube 11 enveloping shaft of endoscope 91 over the portion of shaft 91 that is still outside of the subject's body cavity.

As shown in FIG. 6 adhesive 52 and release sheet 53 and adhesive straps 60 carried by longitudinal edge portions 107 and 108 along entire length of sheet 101 for approximation of the opposed edge portions. Alternatively, the opposed edge portions can be approximated to assemble the seam 51 using spaced magnets 54 (FIG. 7A, 7B), non-spaced magnets 56 (FIG. 8A, 8B), magnet strings 57 (FIG. 9A, 9B, 9C, 9D), magnet string flap 59 (FIGS. 12A, 12B, 12C, 12 D), zipper 190 (FIG. 13A, 13B), toothless zipper 200 (FIG. 14A, 14B) or combination of these means (FIG. 10A, 10B, 11A, 11B) carried by longitudinal edge portions 107 and 108 along entire length of sheet 101.

Handle 19 of the overtube 11 can be grasped by endoscopist the distal end portion 16 of overtube 11 can be pushed into the body cavity using endoscope shaft 91 as a guide. Overtube distal end portion 16 can be advanced so that distal end portion 16 of overtube 11 reaches to endoscope tip 92 within the body cavity so overtube 11 can be viewed through endoscope and then, it is pulled back just a few centimeters, to ensure that the distal end portion 16 of overtube 11 is situated just proximal to endoscope tip 92 within the body cavity.

At this point, inflatable positioning ring 22 at distal end portion 16 of overtube 11 is inflated to secure the position of overtube 11 within the body cavity. This creates a seal between the external surface of the overtube 11 and the body cavity.

At this point, endoscope shaft 91 can be removed or replaced with another endoscope, if desired, while overtube 11 is still within the body cavity.

At this point, inflatable sealing band 32 or 34 of overtube 11 can be inflated to secure the position of endoscope shaft 91 within overtube 11. This creates a seal between the internal surface of the overtube 11 and the endoscope shaft 91.

Distal end portion of occlusion balloon catheter 80 can be inserted into catheter passageway entrance port 65 on catheter passageway port projection 64 and passed through catheter passageway and exit from catheter passageway exit port 61 at distal end portion 16 of overtube 11 inside the body cavity. Then, inflatable occlusion balloon 84 at distal end portion of occlusion balloon catheter 80 can be independently positioned distal to the distal end portion 16 of overtube 11 within the body cavity, distal to the tip of the endoscope 92.

Then, inflatable occlusion balloon 84 can be inflated to secure the position of the occlusion balloon 84. This creates a seal between the occlusion balloon 84 and the body cavity.

As it is depicted in FIG. 16A, an examination compartment 95 can be formed around endoscope tip 92 within the gastrointestinal tract. Examination compartment 95 is formed when inflatable positioning ring 22, inflatable sealing band 32 or 34 (FIG. 5) and occlusion balloon 84 are all inflated and the compartment is filled with air or water.

As it is depicted in FIG. 16A, the compartment 95 can be filled with air or water. The overtube 11 can further include a catheter passageway and a fluid/insufflation conduit (not shown) that terminates distally at two opening 61 and 42 at the distal end 18 of the overtube 11. The fluid/insufflation conduit can be carried by overtube 11 and terminates proximally at the quick connect fitting 140 at the handle 19 of the overtube 11 that connects fluid/insufflation conduit catheter to automated control system 180. Fluid/insufflation conduit can be used to inflate or deflate examination compartment 95 with water or air.

As it is depicted in FIG. 16A, inflated positioning ring 22 can be asymmetric. The inflated positioning ring 22 can be eccentric relative to longitudinal axis of overtube 11 in a way that inflatable positioning ring 22 and overtube external surface 12 create internal tangent circles. The tangent point of these two circles can be at longitudinal seam 51. This allows better sealing created by inflatable positioning ring 22 within the gastrointestinal lumen and also creates an eccentric position for endoscope shaft 91 within the gastrointestinal lumen. This eccentric position of endoscope shaft 91 within the gastrointestinal lumen provides an advantage in maneuverability of endoscope tip 92 within examination compartment 95 in the gastrointestinal lumen particularly when overtube 11 is rotated.

The overtube 11 can carry positioning ring inflation tube (not shown) that connects distally to inflatable positioning ring 22 and terminates proximally to quick connect fitting 140 at the handle 19 of the overtube 11 that can be used to inflate or deflate inflatable positioning ring 22.

Examination compartment 95 can be enlarged or made smaller within the gastrointestinal tract by pulling or pushing the occlusion balloon catheter 80, thereby moving occlusion balloon 84 independent of the overtube 11 and endoscope tip 92. This can be accomplished without need for deflating the occlusion balloon 84. Alternatively, occlusion balloon 84 can be deflated, repositioned, and re-inflated.

Examination compartment 95 can also be moved along the body cavity when the overtube 11, endoscope shaft 91 within overtube 11 and the occlusion balloon catheter 80 are all moved as a single unit in relation to the body. This can be accomplished without deflating occlusion balloon 84, positioning ring 22 or sealing band 32 or 34. This can be performed for better visualization of the body cavity various portion or moving examination compartment 95 to a desired location. Alternatively, occlusion balloon 84, inflatable positioning ring 22 or inflatable sealing band 32 or 34 can be deflated, repositioned, and re-inflated, together or independent of one another.

After forming the compartment 95 within the body cavity, the endoscope tip 92 can be moved independent of the overtube or positioning ring within the examination compartment 95 without need for deflation of the sealing band 32 or 34. Alternatively, sealing band 32 and 34 can be deflated for moving or repositioning endoscope tip 92 at the end of the overtube 11.

Examination compartment 95 can be filled with air or water depending on the procedure application using fluid catheter conduit 42, which terminates in port 146 of the quick, connects fitting 140 (FIG. 3).

As it is depicted in FIGS. 16B-D, the examination compartment 95 can be used as stepping stone for access to the space beyond gastrointestinal lumen through a puncture 96 within the compartment 95. The compartment 95 that is formed around endoscope tip 92 is punctured using endoscopic tools and the endoscope or other surgical instruments are passing through the created opening 96 to access the extra-luminal space through the lumen of the gastrointestinal tract at the level of compartment 95.

As it is depicted in FIG. 17A, examination compartment 95 can also be lavaged while the endoscope shaft 91 is still within the compartment 95, using irrigation tube system 110 and irrigation/drainage port 111. In this case, the sealing band 34 located at the proximal end portion 14 of the overtube 11 is inflated while the sealing band 32 is kept deflated. Then, the irrigation tube system 110 can be connected through irrigation tube connector 113 to irrigation/drainage port 111. Water or other fluid can be purged into and drained from examination compartment 95 using irrigation/drainage port 111 and irrigation tube system 110 while endoscope shaft 91 is still within overtube 11.

Alternatively, examination compartment 95 can be lavaged after removal of the endoscope shaft 91 from the overtube 11 with irrigation solution or water using irrigation tube system 110 and irrigation/drainage port 111 as it is depicted in FIG. 17B. In this figure, it is shown a cap system 114, comprising a removable cap 115 and a string 116 that is connected from one end to cap 115 and on the other end to handle 19 at proximal end portion 14 of overtube 11. Cap 115 can be used to reversibly seal proximal opening 17 of overtube 11. Cap 115 can close the proximal opening 17 of overtube 11 when endoscope shaft 91 is not in overtube 11. As depicted in FIG. 17B, cap 115 can be connected to overtube 11 by a string 116. Those skilled in the arts can understand that string 116 is for convenience only and not critical to the invention. Cap 115 can be an independent feature, or, alternatively, can be attached to device 10 by any suitable means. When in use, after placement of overtube 11 and inflation of positioning ring 22 and occlusion balloon 84, the sealing band 32 and 34 can be deflated and the endoscope 91 can be withdrawn from the overtube 11 and the irrigation tube system 110 can be connected through irrigation tube connector 113 to irrigation/drainage port 111. Water or other fluid can be purged into and drained from examination compartment 95 using irrigation/drainage port 111 and irrigation tube system 110. The cap 114 can be placed at the proximal opening 17 of the overtube 11. Alternatively, examination compartment 95 can be lavaged after removal of the endoscope shaft 91 from the overtube 11 with irrigation solution or water using irrigation tube system 110 without need to use irrigation/drainage port 111 as it is depicted in FIG. 17C. After placement of overtube 11 and inflation of positioning ring 22 and occlusion balloon 84, the sealing band 32 and 34 can be deflated and the endoscope can be withdrawn from the overtube 11. Irrigation tube system 110 can be connected through irrigation tube connector 113 directly to proximal opening 17 of overtube 11, while the irrigation/drainage port 111 is capped by cap 112. Water or other fluid can be purged into and drained from examination compartment 95 using overtube 11 and irrigation tube system 110 while endoscope shaft 91 is not in overtube 11.

The overtube 11 also carries a set of tubes that terminates at midportion 15 of the overtube 11. The suction conduit port 71, flushing port 75, and fenestration holes 77.

The secretions or air at the area proximal to inflated positioning ring 22 can be aspirated using suction conduit port 71 at midportion 15 of overtube 11.

The flushing port 75 can be used to flush water to clean the area proximal to positioning ring 22. The fenestration hole/s can allow a passive passage of fluid, secretion and gas from the lumen of gastrointestinal tract proximal to the inflatable positioning ring 22 to the lumen of the overtube for drainage of the body cavity.

The secretions or air at the area distal to inflated occlusion balloon 84 can be aspirated using occlusion catheter suction tip 89, downstream of occlusion balloon 84.

After completion of the examination, the air or water within examination compartment 95 is drained via fluid/insufflation conduit port 42 or endoscope suction channel. Then, inflated positioning ring 22, inflated sealing band 32 or 34 and inflated occlusion balloon 84 are all deflated, and overtube 11, occlusion balloon catheter 80 as well as endoscope shaft 91 can be removed independently of each other from the body cavity.

The forgoing description and the drawing are illustrative of the invention and are not to be taken as limiting. Still other variants and rearrangements of structural parts are possible without departing from the spirit and scope of this invention and can readily present themselves to those skilled in the art.

As can also be understood by those skilled in the arts, the order of the steps of the method described above is not critical. The spirit of the invention and the method for employing it are found in the individual features of the invention and their use, not the order in which they are used or presented herein; in fact, the user can elect to eliminate certain steps.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions.

Moreover, all statements herein reciting principles, aspects, and aspects of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure.

The scope of the present invention, therefore, is not intended to be limited to the exemplary aspects shown and described herein. Rather, the scope and spirit of present invention is embodied by the appended claims.

The invention claimed is:

1. A method for performing an endoscopic procedure comprising the steps of:
   placing an endoscope shaft within a body cavity at a desired examination point, the endoscope shaft having a proximal end, mid shaft and a distal end, the distal end terminating in an endoscope tip, wherein the endoscope tip is proximal to the desired examination point;
   positioning a segment of a longitudinally opened overtube over the endoscope mid shaft, the overtube including a longitudinal reclosable seam along an entire length of the overtube, an inner surface, an outer surface, a proximal end and a distal end, a positioning ring adjacent the distal end on the outer surface, at least one sealing band on the inner surface, and an independently positionable occlusion catheter terminating in an occlusion balloon; at least one handle at the proximal end and on the outer surface for grasping and manipulation of the overtube within the body cavity;

closing the seam of the segment of the overtube positioned over the endoscope mid shaft to form a longitudinally closed overtube and move the closed overtube over the endoscope shaft as a guide within the body cavity and repeat the closing and moving till the overtube reaches the desired examination point;

inflating the positioning ring to create a seal between the outer surface of the overtube and the body cavity proximal to the endoscope tip, wherein when inflated the positioning ring is expanded asymmetrically around the overtube;

inflating the at least one sealing band independent from the positioning ring, wherein inflating the at least one sealing band creates a seal between an internal surface of the overtube and endoscope shaft;

passing the independently positionable occlusion catheter terminating in the occlusion balloon through a passageway along the overtube to enter the body cavity at the end of the overtube;

manipulating the independently positionable occlusion catheter to a selected point within the body cavity distal to the endoscope tip;

inflating the occlusion balloon to create seal between the occlusion catheter balloon and the body cavity;

creating a sealed examination compartment between the positioning ring, the occlusion balloon and the sealing band surrounding the distal end of the endoscope shaft; and moving the examination compartment by moving the overtube, the endoscope shaft and the occlusion catheter all together back or forth within the body cavity without need for deflation of the occlusion balloon, wherein moving the examination compartment provides a moving workable space within the body cavity.

2. The method of claim 1, wherein placing of the overtube over the endoscope shaft including further steps of:

having an openable sheet having a first edge and opposed to a second edge, each one of the first edge and the second edge further including a closure, the first edge closure and the second edge closure coacting with one another to form an essentially cylindrical overtube, the first edge closure and the second edge closure including adhesive and release sheet, adhesive straps and release sheet, spaced magnets, non-spaced magnets, magnet strings, magnet string flaps, zipper, toothless zipper or combination of these means carried by longitudinal edge portions along entire length to form the longitudinal reclosable seam; and inserting the overtube into the body cavity over the endoscope shaft as a guide while the sheet is partially open at a proximal portion of the overtube and while a distal portion of the overtube is inserted into the body cavity.

3. The method of claim 1 including the further step of:
introducing diagnostic or therapeutic devices into the examination compartment through the overtube or one or more additional catheter passageways in the overtube extending from the proximal end to the distal end of the overtube and used to puncture a hole within a gastrointestinal lumen within examination compartment and being used as a stage for performing intraperitoneal operations beyond a gastrointestinal tract.

4. The method of claim 1, further comprising inflating or deflating air or fluid while monitoring pressure within the occlusion balloon, the sealing band, the positioning ring, and the examination compartment using a set of tubing that connects to an automated control system.

5. The method of claim 1, where the examination compartment is created within a specific portion of the body cavity and provides a non-moving workable space within the specific portion of the body cavity such that the endoscope can move freely and independently within the examination compartment and such that the endoscopic procedure is performed with a steady relationship of the overtube with inflated balloons and the body cavity.

6. The method of claim 5, further comprising:
deflating the sealing band to release the endoscope shaft within the overtube;
removing the endoscope shaft and introducing other surgical tools through lumen of overtube into the examination compartment;
inflating the sealing band to inflate the examination compartment with air or other gas to recreate the examination compartment and monitor pressure within the examination compartment;
puncturing the wall of the gastrointestinal tract using an accessory device;
entering through the examination compartment a surgical tool, accessory device or an endoscope into the peritoneal cavity for performing surgical procedure outside of the gastrointestinal lumen;
removing the surgical tools from the peritoneum;
closing the punctured site at the wall of the gastrointestinal tract; and
removing the surgical tools and overtube from the body cavity.

7. The method of claim 5, including the further steps of:
deflating the sealing band to release the endoscope shaft within the overtube;
removing the endoscope shaft and introducing an echoendoscope through lumen of overtube into the examination compartment;
inflating the sealing band and fill the examination compartment with water and monitor the pressure within the examination compartment; and
performing endoscopic ultrasound of the body cavity and the structures around the body cavity.

8. The method of claim 1, further comprising moving the examination compartment by moving back or forth the overtube, the occlusion balloon with or independent of the endoscope shaft within the body cavity without need for deflation of the occlusion balloon, the sealing band, and the positioning ring to provide a moving workable space within the body cavity and perform endoscopic procedure while there is a steady relationship of the endoscope shaft and inflated occlusion balloon, sealing band, and positioning ring.

9. The method of claim 8, including the further steps of:
deflating the sealing band to release the endoscope shaft within the overtube;
removing the endoscope shaft and introducing an echoendoscope through lumen of overtube into the examination compartment;
inflating the sealing band and fill the examination compartment with water and monitor the pressure within the examination compartment;
performing endoscopic ultrasound of the body cavity and the structures around the body cavity; and
moving the examination compartment along with the echoendoscope while the endoscopic ultrasound images are being captured.

10. The method of claim 1, further comprising performing an endoscopic procedure wherein the inflated occlusion balloon, the sealing band, and the positioning ring wipe an intestinal lumen in a squeegee action in a direction of the moving examination compartment and propel residual fluid and secretions away from the moving examination compartment.

11. The method of claim 1, wherein the occlusion catheter is a double lumen member having a first lumen that communicates with the occlusion balloon for inflating and deflating the occlusion balloon and a second lumen that terminates distal to the examination compartment for aspirating fluid or air distal to the occlusion balloon, or injecting fluid for irrigation purpose distal to the examination compartment.

12. The method of claim 1, further comprising a suction conduit at a midportion of the overtube on an external surface configured to drain air or water from the body cavity accumulated proximal to the positioning ring, and proximal to the examination compartment.

13. The method of claim 12, further comprising at least one hole connecting the outer surface of the overtube to the inner surface of the overtube for passive passage of fluid and gas accumulated at the midportion of the overtube proximal to the examination compartment on the external surface into the lumen of the overtube.

14. The method of claim 1, further comprising at least one flushing port at a midportion of the overtube on an external surface configured to irrigate a lumen of a gastrointestinal tract proximal to the positioning ring, and proximal to the examination compartment.

15. The method of claim 1, wherein at least one sealing band is located on the inner surface at a portion of the proximal end of the overtube, the method further comprising:
  deflating the sealing band to release the endoscope shaft within the overtube;
  removing the endoscope shaft from the body cavity and overtube completely;
  reintroducing another endoscope shaft or therapeutic device into the overtube while the proximal sealing band creates sealing of an irrigation tube connector; and
  inflating the sealing band.

16. The method of claim 1, wherein at least one sealing band is located on the inner surface, at a portion of the distal end of the overtube.

17. The method of claim 1, wherein at least one sealing band is located on the inner surface, at a portion of the proximal end of the overtube proximal to an irrigation/drainage port and further comprising:
  while the sealing band is inflated, connecting an irrigation tube connector to the irrigation/drainage port in the overtube; and
  performing a lavage of the examination compartment.

18. The method of claim 1, further comprising:
  deflating the sealing band to release the endoscope shaft within the overtube;
  removing the endoscope shaft from the body cavity and overtube completely;
  closing the proximal end of the overtube using a proximal end cap;
  connecting an irrigation tube connector to an irrigation/drainage port in the overtube; and
  performing a lavage of the examination compartment.

19. The method of claim 1, further comprising:
  deflating the sealing band to release the endoscope shaft within the overtube;
  removing the endoscope shaft from the body cavity and overtube completely;
  keeping an irrigation/drainage port capped;
  connecting an irrigation tube connector to the proximal of the overtube; and
  performing a lavage of the examination compartment using irrigation solution.

20. The method of claim 1, further comprising:
  suctioning air or fluid from the examination compartment;
  deflating the occlusion balloon and withdrawing the occlusion catheter at least partially through the catheter passageway;
  deflating the positioning ring; and
  withdrawing the endoscope shaft and the overtube from the body cavity independently or together.

* * * * *